United States Patent [19]

Nakahama et al.

[11] Patent Number: 5,712,100
[45] Date of Patent: Jan. 27, 1998

[54] ANTIBODIES TO PEPTIDES HAVING NGF-LIKE ACTIVITY, AND USE THEREOF

[75] Inventors: Kazuo Nakahama; Tsunehiko Fukuda, both of Kyoto; Tsutomu Kurokawa, Hyogo; Ken-Ichi Kuroshima, Osaka, all of Japan

[73] Assignee: Takeda Limited Industries, Ltd., Osaka, Japan

[21] Appl. No.: 448,892

[22] Filed: May 24, 1995

Related U.S. Application Data

[63] Continuation of Ser. No. 350,214, Dec. 6, 1994, which is a continuation-in-part of Ser. No. 41,904, Apr. 2, 1993, abandoned, which is a continuation of Ser. No. 574,431, Aug. 29, 1990, abandoned.

[30] Foreign Application Priority Data

Aug. 28, 1989  [JP]  Japan ................................. 1-218711
May 25, 1990  [JP]  Japan ................................. 2-134058

[51] Int. Cl.$^6$ .................... C12N 15/85; C07K 16/00; G01N 33/53
[52] U.S. Cl. .................... 435/7.1; 435/326; 530/387.9; 530/388.24; 530/389.2
[58] Field of Search .................... 530/387.9, 388.24, 530/389.2; 485/240.27, 172.3, 70.21

[56] References Cited

FOREIGN PATENT DOCUMENTS 0121338  10/1984  European Pat. Off. .

OTHER PUBLICATIONS

Sevier et al., Clin Chem., 27:1794–1806, 1981.
Cathnco et al., J. Neurochem. 50:1003–1010, 1988.
Businaro et al. J. Neurosci Res., 6:89–98, 1981.
Kasaian et al. Biofactors 2:99–104, 1989.
Hu et al. Gene 70:57–65, 1988.
Ullrich et al., Nature, 303, 821 (1983).
Hohn et al, Nature, 344, 339 (1990).
Maisonpierre, Science, 247, 1466 (1990).
Rosenthal et al., Neuron, 4, 767 (1990).
Ernfors et al., Proc. Natl. Acad. Sci. USA, 87, 5454 (1990).
Inoue et al., Seikagaku, 61 (9), 1112, 3a–Ah08 (1989).
Onaka et al., Nippon Nogiekagaku Kaishi, 64 (3)) 335, 2Da5 (1990) and English Translation Thereof.

*Primary Examiner*—Lila Feisee
*Assistant Examiner*—Minh-Tam Davis
*Attorney, Agent, or Firm*—David G. Conlin; George W. Neuner

[57] ABSTRACT

Disclosed are (A) an antibody to a peptide consisting of 8 to 9, or 12 to 14 successive amino acids from a polypeptide having nerve growth factor-like activity, (B) a method for producing the antibody, (C) a cloned hybridoma which produces the antibody, (D) a method for producing the cloned hybridoma, (E) a conjugate of the above mentioned peptide with a carrier protein, and (F) a method for purifying, and a method for detecting and assaying a polypeptide having nerve growth factor-like activity.

4 Claims, 10 Drawing Sheets

Fig. 2

```
         10        20        30        40        50        60
GATTACGTGGGCAGCCCCGTGGTGGCGAACAGAACATCACGGCGGAAACGGTACGCGGAG
AspTyrValGlySerProValValAlaAsnArgThrSerArgArgLysArgTyrAlaGlu
                      -10                                -1  1
         70        80        90       100       110       120
CATAAGAGTCACCGAGGGGAGTACTCGGTATGTGACAGTGAGAGTCTGTGGGTGACCGAC
HisLysSerHisArgGlyGluTyrSerValCysAspSerGluSerLeuTrpValThrAsp
                      10                                 20
        130       140       150       160       170       180
AAGTCATCGGCCATCGACATTCGGGGACACCAGGTCACGGTGCTGGGGGAGATCAAAACG
LysSerSerAlaIleAspIleArgGlyHisGlnValThrValLeuGlyGluIleLysThr
                      30                                 40
        190       200       210       220       230       240
GGCAACTCTCCCGTCAAACAATATTTTTATGAAACGCGATGTAAGGAAGCCAGGCCGGTC
GlyAsnSerProValLysGlnTyrPheTyrGluThrArgCysLysGluAlaArgProVal
                      50                                 60
        250       260       270       280       290       300
AAAAACGGTTGCAGGGGTATTGATGATAAACACTGGAACTCTCAGTGCAAAACATCCCAA
LysAsnGlyCysArgGlyIleAspAspLysHisTrpAsnSerGlnCysLysThrSerGln
                      70                                 80
        310       320       330       340       350       360
ACCTACGTCCGAGCACTGACTTCAGAGAACAATAAACTCGTGGGCTGGCGGTGGATACGG
ThrTyrValArgAlaLeuThrSerGluAsnAsnLysLeuValGlyTrpArgTrpIleArg
                      90                                100
        370       380       390       400       410       420
ATAGACACGTCCTGTGTGTGCCTTGTCGAGAAAAATCGGAAGAACATGAATTGGCATC
IleAspThrSerCysValCysAlaLeuSerArgLysIleGlyArgThrEnd
                     110
        430       440       450       460       470       480
TCTCCCCATATATAAATTATTACTTTAAATTATATGATATGCATGTAGCATATAAATGTT 490       500       510       520       530       540
TATATTGTTTTTATATATTATAAGTTGACCTTTATTTATTAAACTTCAGCAACCCTACAG
```

Fig. 3

```
                                                          TyrAlaGluHisLys
                                                          SerSerSerIlsPro

Ser——HisArgGlyGluTyrSerValCysAspSerGluSerLeuTrpValThrAspLys
IlePheIlsArgGlyGluPheSerValCysAspSerValSerValTrpValGlyAspLys

SerSerAlaIleAspIleArgGlyHisGlnValThrValLeuGlyGluIleLysThrGly
ThrThrAlaThrAspIleThrAspIleLysGlyLysGluValMetValLeuGlyGluValAsnIleAsn

AsnSerProValLysGlnTyrPheTyrArgCysLysGluAlaArgProValLys
AsnSerValPheLysGlnTyrPheLysCysArgAspProAsnProValAsp

AsnGlyCysArgGlyIleAspAspLysHisTrpAsnSerGlnCysLysThrSerGlnThr
SerGlyCysArgGlyIleAspSerLysIleTrpAsnSerTyrCysThrThrThrHisThr

TyrValArgAlaLeuThrSerGluAsnAsnLysLeuValGlyTrpArgTrpIleArgIle
PheValLysAlaLeuThrMetAspGly——LysGlnAlaAlaTrpArgPheIleArgIle

AspThrSerCysValCysAlaLeuSerArgLysIleGlyArg——Thr
AspThrAlaCysValCysValLeuSerArgArgLysArgAla
```

Fig. 5A

GCCATGGTTACTTTTGCCACGATCTTACAGGTGAACAAGGTG
AlaMetValThrPheAlaThrIleLeuGlnValAsnLysVal

ATGTCCATCTTGTTTTATGTGATATTTCTCGCTTATCTCCGTGGCATCCAAGGTAACAAC
MetSerIleLeuPheTyrValIlePheLeuAlaTyrLeuArgGlyIleGlnGly AsnAsn
└─ Signal                                                    └─ Pro
ATGGATCAAAGGAGTTTGCCAGAAGACTCGCTCAATTCCCTCATTATTAAGCTGATCCAG
MetAspGlnArgSerLeuProGluAspSerLeuAsnSerLeuIleIleLysLeuIleGln GCAGATATTTTGAAAAACAAGCTCTCCAAGCAGATGGTGGACGTTAAGGAAAATTACCAG
AlaAspIleLeuLysAsnLysLeuSerLysGlnMetValAspValLysGluAsnTyrGln AGCACCCTGCCCAAAGCTGAGGCTCCCCGAGAGCCGGAGCGGGGAGGGCCCGCCAAGTCA
SerThrLeuProLysAlaGluAlaProArgGluProGluArgGlyGlyProAlaLysSer GCATTCCAGCCAGTGATTGCAATGGACACCGAACTGCTGCGACAACAGAGACGCTACAAC
AlaPheGlnProValIleAlaMetAspThrGluLeuLeuArgGlnGlnArgArgTyrAsn SacII
TCACCGCGGGTCCTGCTGAGCGACAGCACCCCCTTGGAGCCCCCGCCCTTGTATCTCATG
SerProArgValLeuLeuSerAspSerThrProLeuGluProProProLeuTyrLeuMet GAGGATTACGTGGGCAGCCCCGTGGTGGCGAACAGAACATCACGGCGGAAACGGTACGCG
GluAspTyrValGlySerProValValAlaAsnArgThrSerArgArgLysArg TyrAla
                                                         └─Mature
    ScaI
GAGCATAAGAGTCACCGAGGGGAGTACTCGGTATGTGACAGTGAGAGTCTGTGGGTGACC
GluHisLysSerHisArgGlyGluTyrSerValCysAspSerGluSerLeuTrpValThr GACAAGTCATCGGCCATCGACATTCGGGGACACCAGGTCACGGTGCTGGGGGAGATCAAA
AspLysSerSerAlaIleAspIleArgGlyHisGlnValThrValLeuGlyGluIleLys ACGGGCAACTCTCCCGTCAAACAATATTTTTATGAAACGCGATGTAAGGAAGCCAGGCCG
ThrGlyAsnSerProValLysGlnTyrPheTyrGluThrArgCysLysGluAlaArgPro GTCAAAAACGGTTGCAGGGGTATTGATGATAAACACTGGAACTCTCAGTGCAAAACATCC
ValLysAsnGlyCysArgGlyIleAspAspLysHisTrpAsnSerGlnCysLysThrSer CAAACCTACGTCCGAGCACTGACTTCAGAGAACAATAAACTCGTGGGCTGGCGGTGGATA
GlnThrTyrValArgAlaLeuThrSerGluAsnAsnLysLeuValGlyTrpArgTrpIle

Fig. 5B

CGGATAGACACGTCCTGTGTGTGTGCCTTGTCGAGAAAAATCGGAAGAACATGAATTGGC
ArgIleAspThrSerCysValCysAlaLeuSerArgLysIleGlyArgThr***

Aha III         Nsi I
ATCTCTCCCCATATATAAATTATTAC<u>TTTAAA</u>TTATATGAT<u>ATGCAT</u>GTAGCATATAAAT

GTTTATATTGTTTTTATATATTATAAGTTGACCTTTATTTATTAAACTTCAGCAACCCTA

CAGTATATAGGCTTTTTTCTCAATAAAATCAGTGTGCTTGCCTTCCCTCAGGCCTCTCCC

ATCTGTTAAAACTTGTTTTGTGATCCGGCTCTCAGGAGTCACTCTGTAAAATCTGTGTAC

ACCAGTATTTTGCATTCAGTATTGTC

5,712,100

ANTIBODIES TO PEPTIDES HAVING NGF-LIKE ACTIVITY, AND USE THEREOF

This is a continuation of application Ser. No. 08/350,214, filed Dec. 6, 1994, which is a CIP of Ser. No. 08/041,904, filed on Apr. 2, 1993, now abandoned, which is a continuation of Ser. No. 07/574,431, filed Aug. 29, 1990, (abandoned).

BACKGROUND OF THE INVENTION

The present invention relates to an antibody to a peptide including at least 8 successive amino acids of an amino acid sequence represented by formula [1] described below, and relates to hybridomas, methods for producing the same and uses thereof.

Many cell growth factors have been isolated and their structures have been elucidated since the discovery of epidermal growth factor (hereinafter referred to as EGF) and nerve growth factor (hereinafter referred to as NGF).

Cell growth factors are useful for the elucidation of cell differentiation mechanism and cell proliferation mechanism, and some of them, including human EGF, are expected to be useful as medicines. Therefore, studies thereon have become increasingly prevalent in recent years.

As to human NGF, its genomic DNA has been isolated, but has not been expressed in a host cell. Hence, the investigations of producing human NGF in large amounts and of using it have not been advanced.

The present inventors cloned a cDNA sequence coding for a polypeptide (I) which showed about 60% homology to human NGF from human glioma cDNA libraries (Japanese Patent Unexamined Publication No. 1-193654/1989 which corresponds to EP Application No. 90 104 419.8 and U.S. patent application Ser. No. 07/488,696, refer to FIGS. 1 to 4). The polypeptide (I) includes the following amino acid sequence represented by formula [1] in a molecule thereof:

TyrAlaGluHisLysSerHisArgGlyGluTyrSerValCys [1]

AspSerGluSerLeuTrpValThrAspLysSerSerAlaIle

AspIleArgGlyHisGlnValThrValLeuGlyGluIleLys

ThrGlyAsnSerProValLysGlnTyrPheTyrGluThrArg

CysLysGluAlaArgProValLysAsnGlyCysArgGlyIle

AspAspLysHisTrpAsnSerGlnCysLysThrSerGlnThr

TyrValArgAlaLeuThrSerGluAsnAsnLysLeuValGly

TrpArgTrpIleArgIleAspThrSerCysValCysAlaLeu

SerArgLysIleGlyArg

The polypeptide (I) is considered to have an action similar to that of NGF and important roles in vivo such as enhancement of differentiation, growth and proliferation of animal cells, enhanced expression of genes and induction of proteins and enzymes. This polypeptide has therefore the high possibility that it can be used as medicines.

Basic information as to the polypeptide (I) such as the distribution thereof in vivo, the production mode thereof or the mechanism of activity expression favors the development of the polypeptide (I) as medicines.

It is also important to know the amount of the polypeptide (I) exactly, when this protein is purified from a gene recombinant.

Previously, the amount of NGF has been calculated by assaying the neurite outgrowth action to PC12 cells. Also, the neurite outgrowth action to avian dorsal root ganglia has been utilized to calculate the amount of NGF. However, these assays have the disadvantages that the elaborate procedure is required and the measurement error is large, in addition, that a long time is required to obtain the result. For these reasons, it has been desired to develop means of assaying the polypeptide (I) simply and exactly.

SUMMARY OF THE INVENTION

It is therefore an object of the present invention to provide means of assaying the polypeptide (I) simply and exactly. Other objects will be apparent from the following description and appended drawings.

The present invention provides:

(1) an antibody to a peptide including at least 8 successive amino acids of an amino acid sequence represented by formula [1] wherein said antibody has no substantial cross-reactivity with human NGF, (2) the antibody described in (1), in which the antibody is a polyclonal antibody, (3) the antibody described in (1), in which the antibody is a monoclonal antibody, (4) the antibody described in (1), (2) or (3), in which the antibody is obtained by using a conjugate of a peptide with a carrier protein as an immunogen, the peptide including at least 8 successive amino acids of the amino acid sequence represented by formula [1], (5) the antibody described in (1) or (4), in which the peptide is a polypeptide (I) including the amino acid sequence represented by formula [1], (6) the antibody described in (1) or (4), in which the peptide is a partial peptide of the polypeptide (I), the partial peptide consisting of 12 to 14 successive amino acids of a sequence represented by formula [2], Tyr Ala Glu His Lys Ser His Arg Gly Glu Tyr Ser Val Cys, or 8 to 9 successive amino acids of a sequence represented by formula [3], Cys Ala Leu Ser Arg Lys Ile Gly Arg, (7) a method for producing the polyclonal antibody described in (2) which comprises immunizing a mammal with a peptide including at least 8 successive amino acids of the amino acid sequence represented by formula [1] or with a conjugate of the peptide with a carrier protein to form the polyclonal antibody, and then collecting the polyclonal antibody, (8) a method for producing the monoclonal antibody described in (3) which comprises proliferating a cloned hybridoma composed of a spleen cell of a mammal and a lymphoid cell of the mammal in a liquid culture medium or in an peritoneal cavity of the mammal to form and accumulate the monoclonal antibody, the spleen cell of the mammal being immunized with a peptide including at least 8 successive amino acids of the amino acid sequence represented by formula [1] or with a conjugate of the peptide with a carrier protein, and then collecting the monoclonal antibody, (9) A cloned hybridoma composed of a spleen cell of a mammal and a lymphoid cell of the mammal, the spleen cell of the mammal being immunized with a peptide including at least 8 successive amino acids of the amino acid sequence represented by formula [1] or with a conjugate of the peptide with a carrier protein,

(10) a method for producing a cloned hybridoma composed of a spleen cell of a mammal and a lymphoid cell of the mammal, which comprises cell fusing the spleen cell of the mammal with the lymphoid cell thereof to form a fused cell, the spleen cell of the mammal being immunized with a peptide including at least 8 successive amino acids of the amino acid sequence represented by formula [1] or with a conjugate of the peptide with a carrier protein, and then cloning the fused cell,

(11) a partial peptide of the polypeptide (I), the partial peptide consisting of 12 to 14 successive amino acids of the sequence represented by formula [2], Tyr Ala Glu His Lys Ser His Arg Gly Glu Tyr Ser Val Cys.

(12) a partial peptide of the polypeptide (I), the partial peptide consisting of 8 to 9 successive amino acids of the sequence represented by formula [3], Cys Ala Leu Ser Arg Lys Ile Gly Arg,

(13) a conjugate of a peptide including at least 8 successive amino acids of the amino acid sequence represented by formula [1] with a carrier protein,

(14) the conjugate described in (13), in which the peptide is the polypeptide (I) including the amino acid sequence represented by formula [1] in a molecule thereof,

(15) the conjugate described in (13), in which the peptide is the partial peptide described in (11) or (12),

(16) a method for purifying the polypeptide (I) which comprises using the antibody described in (1), (3), (4), (5) or (6), and

(17) a method for detecting and assaying the polypeptide (I) which comprises using the antibody described in (1), (3), (4), (5) or (6).

BRIEF DESCRIPTION OF THE DRAWINGS

FIG. 2 shows a nucleotide sequence of the DNA containing the polypeptide (I) cDNA contained in plasmid pUNK5 obtained in Reference Example 1, and an amino acid sequence translated therefrom;

FIG. 3 shows a comparison of the amino acid sequence (the upper row) of the polypeptide (I) of the present invention described in Reference Example 1 with an amino acid sequence (the lower row) of human NGF;

FIG. 5 shows a nucleotide sequence of the DNA sequence comprising the polypeptide (I) cDNA contained in plasmid pHNT2 obtained in Reference Example 2, and an amino acid sequence translated therefrom;

DESCRIPTION OF THE PREFERRED EMBODIMENT

Figure 1:
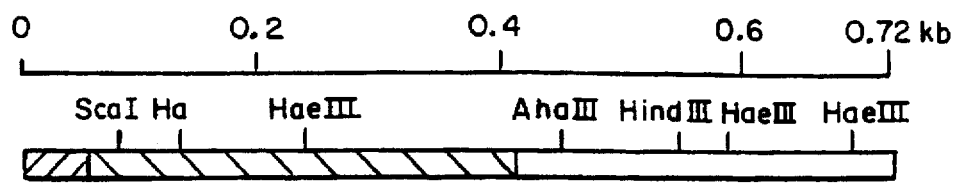
FIG. 1 is a restriction enzyme map of a DNA comprising a polypeptide (I) cDNA contained in plasmid pUNK5 obtained in Reference Example 1.

When the antibodies of the present invention are produced, the polypeptide (I) or its partial peptides can be used as immunogens.

The polypeptide (I) of the present invention includes a polypeptide having the amino acid sequence of formula [1] and a polypeptide further having a threonine residue at the C-terminus of the amino acid sequence of formula [1]. Further, the polypeptide (I) of the present invention includes a polypeptide having several amino acid residues added to the N-terminus and/or the C-terminus of the amino acid sequence of formula [1].

In Reference Examples described below, the polypeptide (I) having the following amino acid sequence represented by formula [1'] in which Thr is added to the C-terminus of the amino acid sequence represented by formula [1] was produced by expression in Escherichia coli.

TyrAlaGluHisLysSerHisArgGlyGluTyrSerValCys [1']

AspSerGluSerLeuTrpValThrAspLysSerSerAlaIle

AspIleArgGlyHisGlnValThrValLeuGlyGluIleLys

ThrGlyAsnSerProValLysGlnTyrPheTyrGluThrArg

CysLysGluAlaArgProValLysAsnGlyCysArgGlyIle

AspAspLysHisTrpAsnSerGlnCysLysThrSerGlnThr

TyrValArgAlaLeuThrSerGluAsnAsnLysLeuValGly

TrpArgTrpIleArgIleAspThrSerCysValCysAlaLeu

SerArgLysIleGlyArg

Further, in Reference Examples described below, the polypeptide (I) expressed in animal cells is believed to have the amino acid sequence represented by formula [1] or [1']

In addition to the polypeptides described above, the polypeptide (I) of the present invention includes portions of the above polypeptides which have the same activity as the above polypeptides, and polypeptides in which portions of the above amino acid sequences are replaced with one or more different amino acids or amino acid sequences, or in which one or more different amino acids or amino acid sequences is added to or inserted into the above amino acid sequences, and which have the same activity as the above polypeptides.

When the polypeptide (I) is produced by using gene recombinant techniques, a methionine residue corresponding to initiation codon ATG upstream from a gene coding for the polypeptide (I) may be added to the N-terminus of the polypeptide (I).

The polypeptide (I) is obtained, for example, by introducing an expression vector containing a DNA coding for the polypeptide (I) into an appropriate host and then cultivating the resulting transformant.

The above expression vector containing a nucleotide sequence coding for the polypeptide (I) can be obtained, for example, by the following process:

(a) RNA coding for polypeptide (I) is isolated.

(b) Single stranded complementary DNA (cDNA) is synthesized from the RNA, followed by synthesis of double stranded DNA.

(c) The complementary DNA is introduced into a plasmid.

(d) A host cell is transformed with the recombinant plasmid thus obtained.

(e) After culturing the transformants thus obtained, the plasmid containing the desired DNA is isolated from the transformants by an appropriate method such as colony hybridization using a DNA probe.

(f) The desired cloned DNA is cut out from the plasmid.

(g) The cloned DNA is ligated downstream from a promoter in the vector.

The RNA coding for the polypeptide (I) can be obtained from various polypeptide (I)-producing cells, for example, human glioma cells, pituicytes and fibroblasts.

The expression vector thus obtained is introduced into appropriate host cells (such as *Escherichia coli*, *Bacillus subtilis*, yeast and animal cells) and the resulting transformants are cultivated, whereby the polypeptide (I) can be produced.

Partial peptides containing at least 8 successive amino acids of the amino acid sequence of the polypeptide (I) can be used as immunogens. Examples of such partial peptides include N-terminal partial peptides consisting of 12 to 14 successive amino acids of a sequence represented by formula [2], Tyr Ala Glu His Lys Ser His Arg Gly Glu Tyr Ser Val Cys and C-terminal partial peptides consisting of 8 to 9 successive amino acids of a sequence represented by formula [3], Cys Ala Leu Ser Arg Lys Ile Gly Arg.

The above partial peptides can be produced by peptide synthesis methods known in the art, which may be any of the known solid phase synthesis methods and liquid phase synthesis methods. Examples of such peptide synthesis methods include the methods described in Schroder and Lubke, *The Peptide*, Vol. 1, Academic Press, New York, U.S.A. (1966), Izumiya et al., *Peptide Synthesis*, Maruzen (1975) and Izumiya et al., *Fundamentals and Experiments of Peptide Synthesis*, Maruzen (1985).

The partial peptides may be produced by cleaving the polypeptide (I) with appropriate enzymes. Such methods include, for example, the method described in *Course of Biochemical Experiments* 1, *Chemistry of Proteins*, pages 255 to 332, edited by Biochemical Society of Japan, Tokyo Kagaku Dojin (1976).

When peptides including at least 8 successive amino acids of an amino acid sequence represented by formula [I] are used for immunization, they may be used as conjugates with carrier proteins.

Examples of the carrier proteins include bovine serum albumin, bovine thyroglobulin, bovine γ-globulin, hemocyanin, and Freund's complete adjuvant (Difco).

The above peptides can be coupled with the carrier proteins by methods known in the art. Reagents used for the coupling include, for example, glutaraldehyde and water-soluble carbodiimide. The weight ratio of the peptide to the carrier protein is suitably about 1:1 to 1:30, preferably about 1:15 to 1:20, more preferably about 1:1 to 1:4. When the reaction is conducted at a pH around neutrality, particularly of approximately 7.3, good results are obtained in many cases. The time required for the reaction is preferably about 2 to 6 hours in many cases, more preferably about 3 hours. The conjugates thus prepared are dialyzed against water at about 4° C. by conventional methods. The resulting products may be stored frozen or lyophilized.

In order to produce the polyclonal antibodies, warm-blooded animals are inoculated with the immunogens prepared as described above. Examples of the warm-blooded animals used for production of the above antibodies include warm-blooded mammals (such as sheep, goat, rabbits, bovines, rats, mice, guinea pigs, horses and pigs) and birds (such as chickens, pigeons, ducks, geese and quail). The immunogens are inoculated into the warm-blooded animals in amounts effective for antibody production. For example, 1 mg of the immunogen per one inoculation is emulsified with 1 ml of physiological saline and Freund's complete adjuvant, and subcutaneously inoculated into the back and hind-limb palm of the rabbit every 4 weeks, 5 times in total, whereby the antibody is produced in many cases. The antibodies thus formed in the warm-blooded animals are collected. For example, in case of the rabbit, the blood is collected from the aural vein usually 7 to 12 days after the final inoculation and subjected to centrifugation to obtain the antibody as a serum. The resulting antiserum is usually subjected to affinity chromatography using a carrier bearing each antigen peptide to recover adsorbed fractions, whereby the polyclonal antibody can be purified.

On the other hand, the monoclonal antibody can also be utilized which is obtained by a method similar to that of Milstein et al. [*Nature* 256, 495 (1975)]. Namely, the monoclonal antibody-producing hybridoma cells of the present invention can be prepared by selecting individuals showing a high antibody titer from the warm-blooded animals, for example, mice, immunized similarly with the above method for preparing the polyclonal antibody, collecting spleens or lymphatic corpuscles therefrom after 2 to 5 days from the final immunization, and fusing antibody-producing cells contained therein with myeloma cells. The fusing procedure can be conducted according to methods known in the art, for example, the method of Kohler and Milstein [*Nature* 256, 495 (1975)]. Fusion accelerators, including polyethylene glycol (PEG) and Sendai virus, may be used. In particular, PEG is preferably used. Examples of the myeloma cells include NS-1, P3U1 and SP2/0, and particularly P3U1 is preferably used. The ratio of the number of the antibody-producing cells to the number f the myeloma cells is preferably about 1:1 to 20:1. PEG (preferably PEG 1,000 to PEG 6,000) is added in a concentration of about 10 to 80%, followed by incubation at 20° to 40° C., preferably 30° to 37° C., for 1 to 10 minutes, whereby cell fusion can be effectively performed.

In order to obtain the monoclonal antibodies of the present invention, it is preferred to use rats or mice for immunization. When the mice are immunized, for example, subcutaneous, intraperitoneal or intravenous injections are preferably used. In particular, subcutaneous injection is preferable. The immunizing interval and the immunizing dose are widely changeable, and various methods are available. For example, methods in which immunization is carried out about 2 to 6 times at intervals of 2 weeks and spleen cells are removed after about 1 to 5 days, preferably about 2 to 4 days from the final immunization are frequently used. As the immunizing dose, it is preferred to use about 0.1 μg or more, preferably about 10 to 300 μg of the peptide per one immunization. Further, it is desirable to carry out the fusion process using the spleen cells after confirmation of an increase in antibody titer in blood by collecting a portion of blood before removal of the spleens.

The above spleen cells are fused with lymphoid cells. For example, the spleen cells removed from the mice are fused with lymphoid cell strains such as suitable myeloma cells [for example, P3-X-63-Ag 8UI (Ichimori et al., *J. Immun. Method* 80, 55 (1985))] of the same kind or a different kind (preferably the same kind) having markers such as hypoxanthine-guanine-phosphoribosyl-transferase deficient (HGPRT⁻) and thymidine kinase deficient (TK⁻). For example, the fused cells are produced in accordance with the method of Kohler and Milstein [*Nature* 256, 495 (1975)]. For example, myeloma cells and spleen cells in a ratio of about 1:5 are suspended in a medium (hereinafter referred to as IH medium) prepared by mixing Iscove medium and Ham F-12 medium in a 1:1 ratio, and a fusion accelerator such as Sendai virus or polyethylene glycol (PEG) is added thereto. It is of course possible to add other fusion accelerators such as dimethyl sulfoxide (DMSO). The polymerization degree of PEG is usually about 1,000 to 6,000, the fusion time is about 0.5 to 30 minutes, and the concentration of the suspension is about 10 to 80%. As a preferred condition, the myeloma cells and the spleen cells are fused with each other in a concentration of about 35 to 55% for about 4 to 10 minutes using PEG 6,000, which results in efficient fusion. The fused cells can be selectively proliferated using hypoxanthine-aminopterin-thymidine medium (HAT medium) [*Nature* 256, 495 (1975)].

The culture supernatant of the proliferated cells is then screened for desired antibody production. The screening of the antibody titer can be carried out in the following manner. First, the presence or absence of the antibody produced by peptide immunization is examined by radio immunoassays (RIAs) or enzyme immunoassays (EIAs). For these methods, various modified methods are also available. As a preferred example of the assays, a method using the EIA is hereinafter described. A rabbit anti-mouse immunoglobulin antibody is coupled with a carrier such as cellulose beads according to conventional methods, and then a culture supernatant or mouse serum to be assayed is added thereto, followed by reaction at a constant temperature (about 4° to 40° C., the same applied hereinafter) for a definite time. After the reaction product is thoroughly washed, an enzyme-labeled peptide (a peptide is coupled with an enzyme according to conventional methods, followed by purification) is added thereto, followed by reaction at a constant temperature for a defined time. After the reaction product is thoroughly washed, an enzyme substrate is added thereto, followed by reaction at a constant temperature for a defined time. Then, the absorbance or fluorescence of the colored product is measured.

It is desirable that the cells in wells which show cell proliferation in a selective medium and antibody activity to the peptide used for immunization are cloned by a limiting dilution analysis. The supernatant of the cloned cells is similarly screened to increase the cells in the wells which show a high antibody titer, whereby monoclonal antibody-producing hybridoma clones showing the reactivity with the immunized peptide can be obtained.

The hybridoma cells thus cloned are proliferated in a liquid medium. Specifically, for example, the hybridoma cells are cultivated in the liquid medium such as a medium prepared by adding about 0.1–40% bovine serum to RPMI-1640 [G. E. Moore et al., *J. Am. Med. Assoc.* 199, 549 (1967)], for about 2 to 10 days, preferably 3 to 5 days, whereby the monoclonal antibody can be obtained from the culture solution. The antibody can further be obtained by intraperitoneally inoculating mammals with the hybridoma cells thereby proliferating the cells and then collecting the ascites. In the case of mouse, for example, about $1 \times 10^4$ to $1 \times 10^7$, preferably $5 \times 10^5$ to $2 \times 10^6$ of the hybridoma cells are intraperitoneally inoculated into a mouse such as BALB/c preliminarily inoculated with mineral oil and the like, and the ascites is collected after about 7 to 20 days, preferably after about 10 to 14 days. The monoclonal antibody formed and accumulated in the ascites can be easily isolated as pure immunoglobulin by ammonium sulfate fractionation, DEAE-cellulose column chromatography or the like.

The monoclonal antibodies which specifically bind to the peptide including at least 8 seccessive amino acids of an amino acid sequence represented by formula [1] are thus obtained.

The monoclonal antibodies of the present invention specifically bind to immunogens, the peptide including at least 8 seccessive amino acids of an amino acid sequence represented by formula [1].

In some cases, the monoclonal antibodies of the present invention bind to the peptide including at least 8 successive amino acids of an amino acid sequence represented by formula [1] which is different from the peptide used as an immunogen when the antibodies are produced.

The monoclonal antibodies of the present invention are monoclonal antibodies to peptides including at least 8 successive amino acids of an amino acid sequence represented by formula [1] which are immunogen peptides.

The monoclonal antibodies of the present invention have the property of specifically binding to the peptide including at least 8 seccessive amino acids of an amino acid sequence represented by formula [1].

The monoclonal antibodies of the present invention have a molecular weight of about 140 to 16 kilodaltons and belong to IgM or IgG in immunoglobulin class.

The molecules of the above antibodies may be fractions thereof, such as F(ab')₂, Fab' or Fab. As the molecule to which a labeling agent described below is directly bound, Fab' is preferred.

The monoclonal antibodies of the present invention are very useful as reagents for assaying the polypeptide (I), because they specifically bind to the polypeptide (I) and have no substantial cross-reactivity with human NGF. It is also very useful from the viewpoint of obtaining basic information (such as distribution in vivo) regarding the polypeptide (I) to make it easy to assay the polypeptide (I) in living organs and tissues. In order to detect the polypeptide (I) in the living organs and tissues, enzyme immunoassays (EIAs), fluorescent antibody methods and radio immunoassays (RIAs) are usually employed. Western blotting analysis may be used to determine the size of the polypeptide (I) in these organs and tissues. In this method, crude extracts derived from the organs or the tissues or partially purified samples thereof are subjected to polyacrylamide gel electrophoresis, followed by transfer to membrane filters to detect the polypeptide (I) with HRP-bound antibodies.

For the antibodies having neutralizing activity, it is also possible to pursue the function of the polypeptide (I) in vivo by neutralizing the activity of the polypeptide (I).

It is further possible to use antibody affinity columns prepared by utilizing the binding ability of the antibodies with the polypeptide (I), as reagents for purifying the polypeptide (I).

The EIA or the RIA used to detect and assay the polypeptide (I) is carried out, for example, in the following manner. The purified antibody is fixed in an amount of 0.1 to 10 μg/well to a carrier such as a 96-well plastic plate (for example, Immunoplate, Nunc, Denmark), glass beads or plastic beads. In the case of the plastic plate or the plastic beads, the antibody is fixed by reaction at 4° C. overnight or at room temperature for about 0.5 to 4 hours. In the case of the glass beads, the antibody is fixed, for example, by a method as described in Proc. Natl. Acad. Sci. U.S.A. 80, 3513-3516 (1983). Various other plates for fixation of antibodies, which are commercially available, can also be used.

A solution containing the antigen polypeptide (I) is added to the plate of the beads to which the antibody is thus fixed, followed by adsorption reaction. The adsorption reaction is sometimes conducted at room temperature for about 0.2 to 2 hours, however preferably conducted at about 4° C. overnight.

After the antigen-antibody binding reaction, an antibody to which a labeling agent is bound is added, followed by adsorption reaction. The labeling agents include radioisotopes, enzyme, fluorescent substances and luminous substances. However, it is preferred to use the enzymes. As the enzymes, which are preferably stable and high in specific activity, there can be used peroxidases, alkaline phosphatases, β-D-galactosidases, glucose oxidases and the like. In particular, peroxidases are preferably used. Peroxidases of various origins can be used. Examples of such peroxidases include peroxidases obtained from horseradishes, pineapples, figs, sweet potatoes, broad beans and cone. In particular, horseradish peroxidase (HRP) extracted from horseradishes is preferable.

In binding peroxidase to the antibody, the thiol group of Fab' is utilized as the antibody molecule. For this reason, peroxidase into which a maleimide group is preliminarily introduced is conveniently used.

When a maleimide group is introduced into peroxidase, a maleimide group can be introduced through an amino group of the peroxidase. For this purpose, N-succinimidyl-maleimide-carboxylate derivatives can be used. N-(γ-maleimidobutyloxy) succinimide (hereinafter also referred to as GMBS for brevity) is preferably used. A certain group may therefore intervene between the maleimide group and the peroxidase.

GMBS is reacted with peroxidase in a buffer solution having a pH of 6 to 8 at about 10° to 50° C. for about 10 to 24 hours. The buffer solutions include, for example, 0.1M phosphate buffer (pH 7.0). The maleimidated peroxidase thus obtained can be purified, for example, by gel chromatography. Examples of carriers used in the gel chromatography include Sephadex G-25 (Pharmacia Fine Chemical, Sweden) and Biogel P-2 (Bio RAD Laboratories, U.S.A.).

The maleimidated peroxidase can be reacted with an antibody molecule in a buffer solution at about 0° to 40° C. for about 1 to 48 hours. The buffer solutions include, for example, 0.1M phosphate buffer (pH 6.0) containing 5 mM sodium ethylenediaminetetraacetate. The peroxidase-labeled antibody thus obtained can be purified, for example, by gel chromatography. Examples of carriers used in the gel chromatography include Sephadex G-25 (Pharmacia Fine Chemical, Sweden) and Biogel P-2 (Bio RAD Laboratories, U.S.A.).

A thiol group may be introduced into the peroxidase to react with the maleimidated antibody molecule.

Enzymes other than the peroxidases can be directly bound to the antibodies similarly to the methods of binding the peroxidases, and known methods which achieve such binding include, for example, the glutaraldehyde method, the periodic acid method and the water-soluble carbodiimide method.

For the enzyme-labeled antibodies, reaction substrates such as 2,2'-diadino-di[3-ethylbenzothiazoline sulfonate(6)] in the case of HRP are added to develop color, thereby measuring absorbance. As to the radio-labeled antibodies, the radioactivity of the antibodies not bound to the polypeptide (I) is measured by a scintillation counter. The absorbance or the radioactivity of the samples are compared to the values to the polypeptide (I) of a known amount, whereby the polypeptide (I) can be assayed.

In addition to sandwich EIAs in which an antigen is sandwiched between two kinds of antibodies and which is described later, competitive EIAs and indirect EIAs which are well known are carried out. In the competitive EIAs, the antibody is fixed to a carrier, and the enzyme- or radio-labeled antigen polypeptide (I) and a sample is added thereto, followed by reaction and assay of the polypeptide (I). The reaction and estimation of the labeled antigen are conducted under the conditions similar to those described above. In the indirect EIAs, a test sample is reacted with the antibody which is not fixed to a carrier, and the antibody which is not adsorbed is assayed with a plate to which the antigen is fixed and an anti mouse-labeled antibody. The reaction and the measurement of the radioactivity are conducted under the conditions similar to those described above.

Test samples used in the assay system, such as the detection and determination of the polypeptide (I) of the present invention, include humors such as urine, serum, plasma and cerebrospinal fluid, extracts of animal cells, and culture supernatants thereof.

As an example of the assays of the present invention, a case is hereinafter described in detail in which the peroxidase is used as the labeling agent, but the present invention is not limited to the peroxidase.

(1) First, a test sample containing the polypeptide (I) to be assayed is added to the antibody held on a carrier to conduct antigen-antibody reaction, and then the conjugate of the peroxidase with the antibody obtained above is added thereto, followed by reaction.

Test samples used in this assay system include humors such as urine, serum, plasma and cerebrospinal fluid, extracts of animal cells, and culture supernatants thereof.

The carriers on which the antibody is held in the assays of the polypeptide (I) include, for example, gel particles such as agarose gels [for example, Sepharose 4B and Sepharose 6B (Pharmacia Fine Chemical, Sweden)], dextran gels [for example, Sephadex G-75, Sephadex G-100 and Sephadex G-200 (Pharmacia Fine Chemical, Sweden)] and polyacrylamide gels [for example, Biogel P-30, Biogel P-60 and Biogel P-100 (Bio RAD Laboratories, U.S.A.)]; cellulose particles such as Avicel (Asahi Chemical Industry, Japan) and ion exchange cellulose (for example, diethylaminoethyl cellulose and carboxymethyl cellulose); physical adsorbents such as glass (for example, glass balls, glass rods, aminoalkyl glass balls and aminoalkyl glass rods), silicone pieces, styrenic resins (for example, polystyrene balls and polystyrene particles) and plates for immunoassay (for example, Nunc, Denmark); and ion exchange resins such as acescent cation exchange resins [for example, Amberlite IRC-50 (Rohm & Haas, U.S.A.) and Zeocurve 226 (Permutit, West Germany)], and alkalescent anion exchange resins (for example, Amberlite IR-4B and Dowex (Dow Chemical, U.S.A.)].

In order to hold the antibody on the carrier, methods known in the art are applied. Examples of such methods include the cyanogen bromide method and the glutaraldehyde method which are described in *Metabolism* 8, 696 (1971). As a simpler method, the antibody may be adsorbed on the surface of the carrier.

(2) The substrate of the peroxidase is added to the reaction product obtained in (1), and then the absorbance or the fluorescent intensity of the resulting substance is measured, thereby knowing the enzyme activity of the above reaction product.

(3) The procedures described in (1) and (2) are preliminarily carried out for the standard solution of the polypeptide (I) of a known amount to prepare a standard curve showing the relation between the amount of the polypeptide (I) and the absorbance or the fluorescent intensity thereof.

(4) The absorbance or the fluorescent intensity obtained for the test sample containing the polypeptide (I) of an unknown amount is applied to the standard curve to determine the amount of the polypeptide (I) in the test sample.

The above antibody can be utilized for the detection and determination of the polypeptide (I) by Western blotting [W. N. Burnette, *Analytical Biochemistry* 112, 195 (1981)].

A specific example of Western blotting is described below.

A sample containing the polypeptide (I) is dissolved for example, in sample buffer [U. K. Laemmli, *Nature* 227, 680 (1970)]. In this case 2-mercaptoethanol is either added thereto as a reducing agent (under reducing conditions) or not (under non-reducing conditions). Either of these conditions may be used. The resulting solution is heated at about 100° C. for 5 minutes, and then subjected to electrophoresis. Any electrophoresis may be used as long as the protein can be separated. Specific examples of such electrophoresis include SDS-polyacrylamide gel electrophoresis. The protein is transferred from the gel after electrophoresis to a nitrocellulose membrane. This method is well known in the art, and includes, for example, the method of Burnette [*Analytical Biochemistry* 112, 195 (1981)]. Then, the polypeptide (I) on the nitrocellulose membrane is detected by an immunological method. Namely, the nitrocellulose membrane is blocked, for example, with a 3% gelatin solution, followed by a first antibody reaction. An antibody used as a first antibody may be either antiserum or a purified antibody. However, the purified antibody is more preferable. As to the conditions of the first antibody reaction after blocking, any set of conditions may be applied as long as the polypeptide (I) on the membrane can be bound to the first antibody. For example, the first antibody reaction is conducted at room temperature for about 4 to 16 hours. After the above first antibody reaction, a second antibody reaction is carried out. As to the second antibody used, any antibody can be employed as long as it can be bound to the first antibody and is detectable. Examples of such antibodies include IgG coupled with a labeling enzyme. Specific examples of labeling enzymes include horseradish peroxidase (HRP) and alkaline phosphatase. As to the conditions of the first antibody reaction, any conditions may be applied as long as the second antibody can be bound to the first antibody. For example, the second antibody reaction is conducted at room temperature for about 1 hour. After the above second antibody reaction, color is developed and the band of the polypeptide (I) on the nitrocellulose membrane is detected. According to the above Western blotting, the polypeptide (I) is detectable if it exists in an amount of about 50 ng or more. The polypeptide (I) in the test sample can be determined by comparing the density of the band of the test sample to the density of the bands of a known amount of polypeptide (I). In lieu of the above first antibody, for example, the conjugate of the antibody with HRP may be used.

In order to purify the polypeptide (I), the purified antibody is coupled with a suitable carrier such as activated agarose gel beads according to conventional methods, and packed in a column. Then, a sample containing the polypeptide (I), such as a culture supernatant or disrupted cells, is loaded onto the antibody column to allow the sample to be adsorbed thereby, followed by washing. Then, elution is carried out with a chaotropic reagent such as potassium thiocyanate (KSCN) or under such acescent conditions that the polypeptide (I) is not inactivated. Thus, the polypeptide (I) can be efficiently purified.

The antibody column can be prepared by coupling the monoclonal antibody of the present invention, which is, for example, purified from ascites or other humors inoculated with the hybridoma cells, with an appropriate carrier.

Any carrier may be used as long as the polypeptide (I) is specifically efficiently adsorbed thereby after coupling and suitable elution is thereafter possible. By way of example, agarose gel beads in which primary amines of the protein are activated so as to be easily bindable, such as Affi-Gel 10 (Bio RAD), are conveniently used according to the following method. The antibody is reacted with Affi-Gel 10 in a buffer solution such as a bicarbonate solution having a concentration of about 0.001 to 1M, preferably about 0.1M. The reaction is conducted at about 0° to 20° C. at a broad pH range for about 10 to 24 hours, preferably at about 4° C. at a pH of about 7 to 10 for about 4 hours. With respect to the mixing ratio of the antibody to Affi-Gel 10, the larger amount of antibody mixed with Affi-Gel 10, the larger amount of antibody which becomes bound thereto. Up to about 50 mg of antibody per 1 ml of Affi-Gel 10 can become bound. Hence, about 10 to 30 mg of the antibody is conveniently used, considering the purification efficiency in affinity chromatography. The antibody-carrier combined material thus formed is thoroughly washed with the buffer solution used for the reaction. Then, residual unreacted active groups are blocked by allowing the washed material to stand for several days, by adding a compound containing a primary amine such as ethanolamine-hydrochloric acid or glycine thereto to a final concentration of about 0.05 to 0.10M, followed by reaction at about 4° C. for about 1 to 4 hours, or by reacting a protein such as 1 to 5% bovine serum albumin (BSA) therewith at 4° C. overnight. The combined material thus treated is packed in an appropriate column to form the antibody column.

In purifying a sample with the above antibody column, the polypeptide (I) protein-containing sample is dissolved in a buffer solution having a pH around neutrality such as phosphate buffer or Tris-hydrochloric acid buffer, followed by adsorption by the antibody column. Then, the column is washed with the same buffer, and then the polypeptide (I) is eluted. As eluents, the following solutions are commonly used: acetic acid solutions, solutions containing polyethylene glycol, solutions containing peptides more easily bindable with the antibody than the sample, high concentration salt solutions and their combined solutions. Solutions which do not so promote the inactivation of the polypeptide (I) are preferred.

Effluents are neutralized with buffer solutions by methods known in the art. The above purification procedure can be repeated as needed.

Further, the substantially pure polypeptide (I) substantially free from pyrogens and endotoxins can be obtained by combining various purification techniques known in the art. The substantially pure polypeptide (I) of the present invention contains the polypeptide (I) in a concentration of 90% (w/w) or more, preferably 95% (w/w) or more.

The polypeptide (I) protein solution obtained here is subjected to dialysis, and can be pulverized by lyophilization as needed. In lyophilizing, stabilizing agents such as sorbitol, mannitol, dextrol, maltose and glycerol can be added.

When the polypeptide (I) thus obtained has sufficient activity, it is used as is. When it does not have sufficient activity, it can be sufficient activated by enzymatic methods or non-enzymatic methods. The polypeptide (I) thus obtained shows stimulation of differentiation or proliferation of animal cells, particularly of nerve cells, and has inducing activity for various proteins and enzymes. The polypeptide (I) is therefore expected to be used to treat nerve-related pathologic conditions such as nerve lesion.

Further, the polypeptide (I) is expected to have the same action as NGF or action similar to that of NGF.

The polypeptide (I) of the present invention is useful as reagents for studies relating to differentiation, growth, multiplication and survival of animal cells.

When the polypeptide (I) is used as medicine, it can be safely administered parenterally or orally to warm-blooded mammals (such as humans, mice, rats, hamsters, rabbits, dogs and cats) in a powder form as is, or as pharmaceutical preparations together with pharmaceutically acceptable carriers, excipients or diluents.

The injections of the polypeptide (I) are prepared, for example, using physiological saline or aqueous solutions containing glucose or other adjuvants by methods known in the art. The pharmaceutical preparations such as tablets and the capsules can also be prepared.

When the polypeptide (I) is used as the above medicines, it is administered, for example, to the above warm-blooded animals in an appropriate amount ranging from about 1 ng/kg to 100 µg/kg daily, taking into account the route of administration, symptoms, etc.

When the polypeptide (I) is used as the reagents for studies relating to differentiation, growth, proliferation, activation and the like of animal cells, it is preferably added to a culture medium for animal cells in an amount of about 0.1 to 1,000 ng per milliliter of medium, more preferably about 1 to 100 ng per milliliter of medium. The differentiation, growth, proliferation and survival of animal cells can be assayed by incubating animal cells in the medium to which the polypeptide (I) is added.

By using the antibodies to the polypeptide (I) or its partial peptides, the isolation, purification and assay of the polypeptide (I) can be efficiently carried out, and the application of the polypeptide (I) is achieved.

When bases, amino acids and so on are indicated by the abbreviations in this specification and drawings, the abbreviations adopted by IUPAC-IUB Commission on Biochemical Nomenclature or commonly used in the art are employed. For example, the following abbreviations are used. When the optical isomer is capable of existing with respect to the amino acids, the L-form is represented unless otherwise specified.

TABLE 1

| DNA | Deoxyribonucleic acid |
|---|---|
| A | Adenine |
| C | Cytosine |
| G | Guanine |
| T | Thymine |
| Ala | Alanine |

TABLE 1-continued

| Arg | Arginine |
|---|---|
| Asn | Asparagine |
| Asp | Aspartic acid |
| Cys | Cysteine |
| Gln | Glutamine |
| Glu | Glutamic acid |
| Gly | Glycine |
| His | Histidine |
| Ile | Isoleucine |
| Leu | Leucine |
| Lys | Lysine |
| Met | Methionine |
| Phe | Phenylalanine |
| Pro | Proline |
| Ser | Serine |
| Thr | Threonine |
| Trp | Tryptophan |
| Tyr | Tyrosine |
| Val | Valine |
| Boc | t-Butyloxycarbonyl |
| MeBzl | p-Methylbenzyl |
| Bzl | Benzyl |
| -P | Polystyrene resin for solid synthesis of peptide |
| PAM | p-Oxymethylphenylacetamidomethyl resin |
| AcOH | Acetic acid |
| OBzl | Benzyl ester |
| Tos | Tosyl |
| Br-z | 2-Bromobenzyloxycarbonyl |
| Cl-z | 2-Chlorobenzyloxycarbonyl |

Transformant *Escherichia coli* MV1184/pUNK5 obtained in Reference Example 1 described below was deposited with the Institute for Fermentation, Osaka, Japan (IFO) under the accession number IFO 14832 on Feb. 10, 1989. This microorganism was also deposited with the Fermentation Research Institute, Agency of Industrial Science and Technology, Ministry of International Trade and Industry, Japan (FRI) under the accession number FERM BP-2304 on Feb. 22, 1989.

Transformant *Escherichia coli* BL21(DE3)/pLysS, pENGFT102 obtained in Reference Example 8 described below was deposited with the Institute for Fermentation, Osaka, Japan (IFO) under the accession number IFO 14903 on Jul. 14, 1989. This microorganism was also deposited with the Fermentation Research Institute, Agency of Industrial Science and Technology, Ministry of International Trade and Industry, Japan (FRI) under the accession number FERM BP-2529 on Jul. 26, 1989.

Mouse N4-2 cells, mouse N46-31 cells, mouse N82-4 cells and mouse N148-62 cells obtained in Example 2(3) described below were deposited with the Institute for Fermentation, Osaka, Japan (IFO) on Apr. 25, 1990, and with the Fermentation Research Institute, Agency of Industrial Science and Technology, Ministry of International Trade and Industry, Japan (FRI) on May 15, 1990, under the following accession numbers.

| | IFO | FERM BP |
|---|---|---|
| MoAb4-2 | 50241 | 2908 |
| MoAb46-31 | 50242 | 2909 |
| MoAb82-4 | 50243 | 2910 |
| MoAb148-62 | 50244 | 2911 |

The present invention will hereinafter be described in detail with the following Reference Examples and Examples. It is understood of course that these Reference Examples and Examples are not intended to limit the scope of the invention.

REFERENCE EXAMPLE 1

(Cloning of Polypeptide (I) cDNA)

*E. coli* Y1090 was infected with the human glioma-derived λgt11 cDNA libraries (Clontech Laboratories, Inc.) and then about $6 \times 10^5$ phages were spread on an agar plate containing NZCYM medium described in *Molecular Cloning, A Laboratory Manual*, Cold Spring Harbor Laboratory (1982), followed by cultivation at 37° C. for 5 hours. Then, a nylon membrane was placed on the plate, and removed after standing for 1 minute. This nylon membrane was soaked in 0.5M NaOH- 1.5M NaCl, then in 1.5M NaCl-0.5M Tris-HCl (pH 8.0), and further in 2×SSC [Refer to *Molecular Cloning, A Laboratory Manual*, Cold Spring Harbor Laboratory (1982)]. After air drying, the membrane was allowed to stand at 80° C. for 2 hours.

A DNA (about 0.38 kb) coding for human βNGF [Nature 303, 821 (1983)] was chemically synthesized and labeled with [α-$^{32}$P]dCTP by nick translation, thereby preparing a probe.

Using the nylon membrane and the probe obtained in the above, hybridization was carried out according to the method described in *Molecular Cloning, A Laboratory Manual*, Cold Spring Harbor Laboratory (1982). Thus, the nylon membrane was soaked in a hybridization solution containing the probe, and maintained at 65° C. for 16 hours. The nylon membrane was washed with 2×SSC-0.1% SDS at room temperature, and then with 1×SSC-0.1% SDS at 60° C. Thereafter, positive clones were detected by autoradiography.

A cDNA portion was cut out with EcoRI from the clone λβGN1321 thus obtained and inserted into the EcoRI site of plasmid pUC118 (Takara Shuzo) to obtain plasmid pUNK5. Using the plasmid pUNK5 thus obtained, *E. coli* MV1184 (Takara Shuzo) was transformed to obtain transformant *E. coli* MV1184/pUNK5 (IFO 14832, FERM BP-2304).

FIG. 1 shows the restriction enzyme map of the cDNA portion including the polypeptide (I) cDNA contained in the plasmid pUNK5 and having a whole length of about 0.78 kb. In FIG. 1, ☐ shows an untranslated region, ▨ shows a propeptide code region, and ▤ shows a region coding for a polypeptide further having a threonine residue at the C-terminus of the amino acid sequence of formula [1].

The nucleotide sequence of the cDNA portion obtained in the above was determined by the dideoxy method [Messing et al., *Nucl. Acid. Res.* 9, 309 (1981)]. FIG. 2 shows the determined nucleotide sequence and the amino acid sequence translated thereby. In FIG. 2, the region extending from position 1 to the N-terminus of the amino acid sequence is a portion of the propeptide, and the region of positions 1 to 118 and positions 1 to 119 show the polypeptide having the amino acid sequence of formula [1] and the polypeptide further having a threonine residue at the C-terminus of the amino acid sequence of formula [1], respectively.

FIG. 3 shows the amino acid sequence of the polypeptide (I) determined by the above method, in comparison with the amino acid sequence of the human βNGF described in Ullrich et al., *Nature* 303, 821 (1983). In FIG. 3, the upper row indicates the sequence of 119 amino acids of the polypeptide (I), and the lower row indicates the amino acid sequence of the human βNGF. The same amino acid residue portions are boxed In the figure, "–" only shows a chemical bond.

As apparent from this comparison, the sequence of 119 amino acids of the polypeptide (I) of the present invention has a homology of about 60% with the amino acid sequence of the above human βNGF.

Further, when the sequence of 119 amino acids of the polypeptide (I) determined as described above is compared with the amino acid sequence of the mouse βNGF shown in Angeletti et al., *Proceedings of National Academy of Sciences, U.S.A.* 68, 2417 (1971) and Scott et al., *Nature* 302, 538 (1983), it has a homology of about 60%.

REFERENCE EXAMPLE 2

(Recloning of Polypeptide (I) cDNA)

Figure 4:
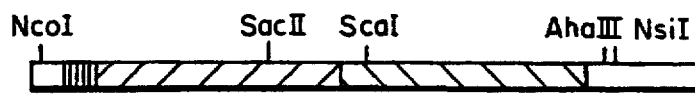
FIG. 4 is a restriction enzyme map of a DNA comprising a polypeptide (I) cDNA contained in plasmid pHNT2 obtained in Reference Example 2.

Using the EcoRI-AhaIII fragment containing the 5'-terminal side of the polypeptide (I) cDNA portion contained in the pUNK5 obtained in Reference Example 1 as a probe, one of the human glioma-derived cDNA libraries (Clontech Laboratories, Inc.) was cloned in a manner similar to that of Example 1. A cDNA portion was cut out with EcoRI from one of many positive clones, λHNT31, thus obtained, was inserted into the EcoRI site of plasmid pUC119 (Takara Shuzo) to obtain plasmid pHNT2. FIG. 4 shows the restriction enzyme map of a polypeptide (I) cDNA (about 1.1 kb) inserted into the plasmid pHNT2. In FIG. 4, ☐ shows a signal peptide code region, ▨ shows a propeptide code region, and ▤ shows a region coding for a polypeptide further having a threonine residue at the C-terminus of the amino acid sequence of formula [1].

The nucleotide sequence of the cDNA portion obtained in the above was determined by the dideoxy method. FIG. 5 shows the determined nucleotide sequence and the amino acid sequence translated thereby. In FIG. 5, "Signal" indicates the signal peptide, "Pro" indicates the propeptide and "Mature" indicates the polypeptide (I) (mature protein).

REFERENCE EXAMPLE 3

(Construction of Polypeptide (I) Expression Vector for *Escherichia coli*)

The polypeptide (I) cDNA inserted into the plasmid pUNK5 obtained in Reference Example 1 has an ScaI site near the region coding for the 11th tyrosine residue from the N-terminus of the polypeptide (I), and an NsiI site downstream from a terminating codon of the polypeptide (I) by 50 bases (refer to FIGS. 2, 4 and 5). A 0.3-kb ScaI-NsiI segment was isolated from the plasmid pUNK5, and adapters NGFTE-1 (35mer), NGFTE-2 (33mer), NGFTE-3 (7mer) and NGFTE-4 (15mer) were ligated thereto with T4 DNA ligase, followed by treatment with restriction enzymes NdeI and BamHI. Thus, a 0.3-kb NdeI-BamHI fragment was obtained (refer to FIG. 6).

These adapters are as follows:

NGFTE-1: 5' TATGTACGCGGAGCATAAGAGTCACCGAGGGGAGT 3'  35 mer

NGFTE-2: 5' ACTCCCCTCGGTGACTCTTATGCTCCGCGTACA 3'  33 mer

NGFTE-3: 5' TGCCAGG 3'  7 mer

NGFTE-4: 5' GATCCCTGGCATGCA 3'  15 mer

The expression vector pET-3C having a T7 promoter [Rosenberg et al., Gene 56, 125 (1987)] was similarly cleaved with NdeI and BamHI to isolate a 4.4-kb NdeI-BamHI fragment.

Figure 6:
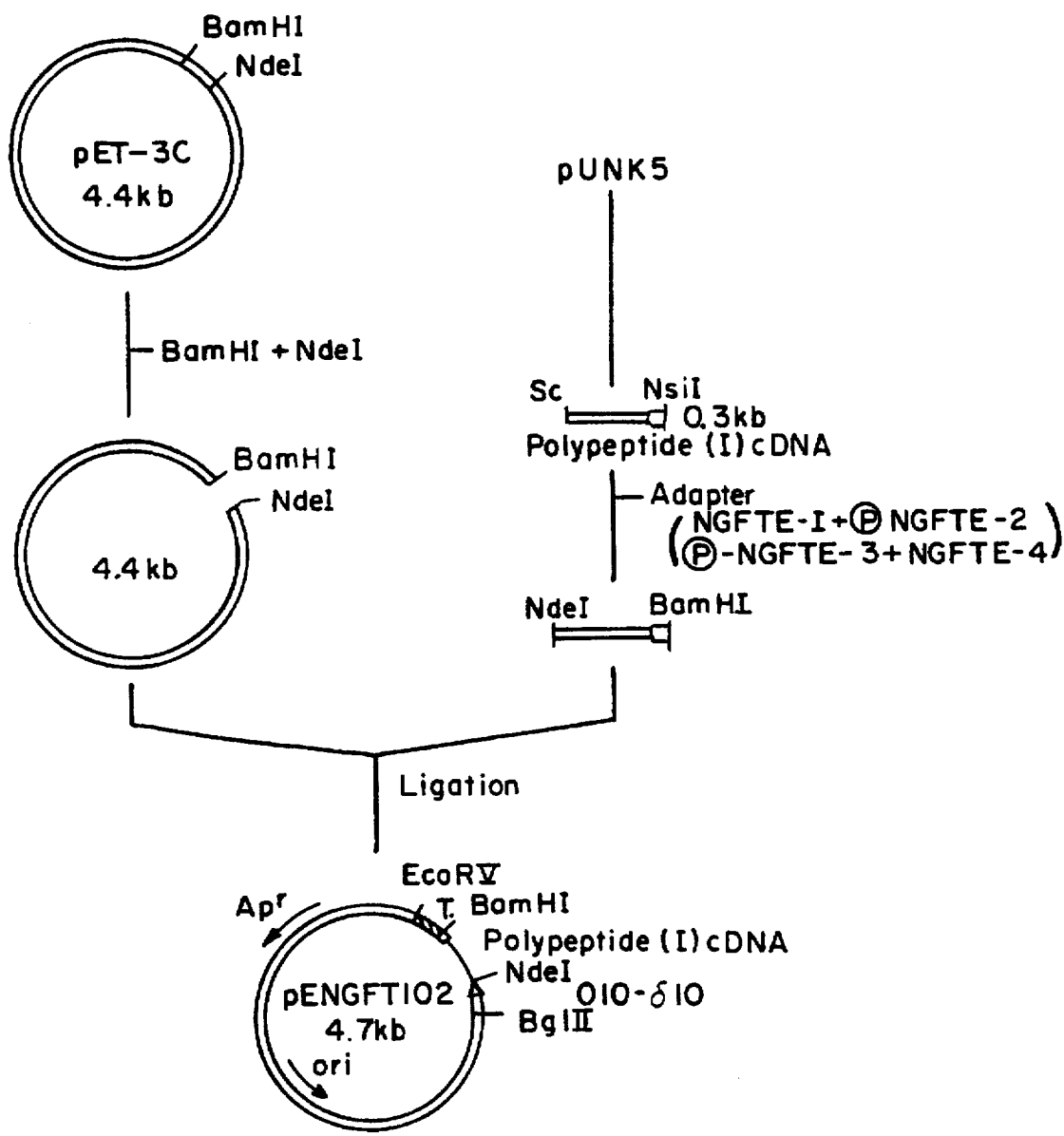
FIG. 6 is a schematic representation showing the construction of polypeptide (I) expression vector pENGFT102 for Escherichia coli obtained in Reference Example 3.

The 4.4-kb NdeI-BanHI fragment obtained above was ligated to the 0.3-kb NdeI-BamHI fragment with T4 DNA ligase, and then the ligated fragment was inserted into E. coli DH1 to prepare a transformant. A plasmid isolated from the resulting ampicillin-resistant transformant strain [E. coli DH1/pENGFT102] was named pENGFT102 (FIG. 6).

REFERENCE EXAMPLE 4

(Preparation and Expression of Transformant)

Using the polypeptide (I) expression vector pENGFT102 obtained in Reference Example 3, E. coli BL21(DE3) [Gene 56, 125 (1987)] was transformed to obtain transformant E. coli BL21(DE3)/pENGFT102.

The transformant E. coli BL21(DE3)/pENGFT102 was cultivated on 5 ml of LB culture medium containing 50 µg/ml ampicillin and 0.2% glucose in a test tube at 37° C. for 16 hours. 1 ml of the resulting culture was transferred into a 200-ml flask containing 20 ml of the same medium, and cultivated at 37° C. When the Klett value reached 170 to 200, IPTG was added thereto to give a final concentration of 0.4 mM, and the cultivation was further continued for 3 hours. Cells collected from 30 µl of the resulting culture were suspended in 30 µl of sample buffer [50 mM Tris-HCl (pH 6.8), 2 mM EDTA, 1% SDS, 1% mercaptoethanol, 8% glycerol, 0.025% Bromophenol Blue1, and heated for 5 minutes, followed by electrophoresis on 16% polyacrylamide gels containing 0.1% SDS. After electrophoresis, the gels were dyed with Coomassie Brilliant Blue. As a result, a 15-kilodalton (kDa) protein which was not detected in E. coli BL21(DE3)/pET-3C obtained by transforming E. coli BL21(DE3) by the above vector pET-3C, was detected in E. coli BL21(DE3)/pENGFT102. The amount of the 15-kDa protein produced was about 10% of the total proteins. This protein was also detected by the Western blotting method using rabbit anti-mouse NGF antibody (Collaborative Research, Inc. U.S.A.).

REFERENCE EXAMPLE 5

(Construction of Polypeptide (I) Expression Vector for Animal Cells)

A 1.1-kb EcoRI fragment containing the polypeptide (I) cDNA was isolated from the plasmid pHNT2 obtained in Reference Example 2. Expression vector pTB389 (described in Japanese Patent Unexamined Publication (Laid-open) No. 64-2572/1989 corresponding to EP-251,244A) was similarly cleaved with EcoRI. The resulting fragment was ligated to the above 1.1-kb EcoRI fragment containing the polypeptide (I) cDNA with T4 DNA ligase, and then the ligation mixture was used for the transformation of E. coli DH1 (Molecular Cloning A Laboratory Manual, Cold Spring Harbor Laboratory, p.505, 1982). A plasmid was isolated from the resulting ampicillin-resistant transformant [E. coli DH1/pNTK26], and this plasmid was named pNTK26.

Figure 7:
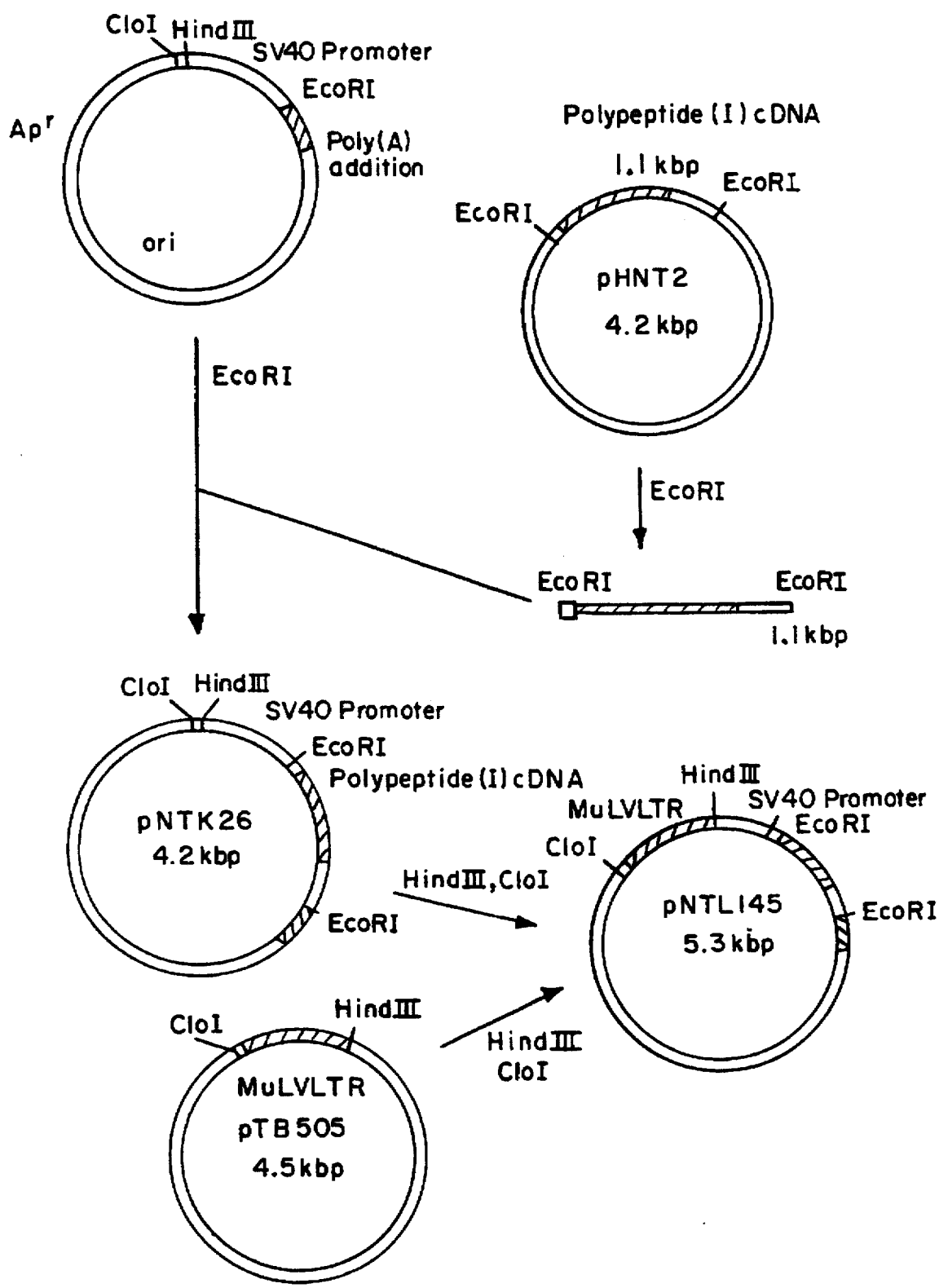
FIG. 7 is a schematic representation showing the construction of polypeptide (I) expression vectors pNTK26 and pNTL145 for animal cells obtained in Reference Example 5.

A 1.1-kb ClaI-HindIII fragment containing an Abelson Mouse leukemia virus (A-MuLV) LTR region was isolated from plasmid pTB505 (described in Japanese Patent Unexamined Publication (Laid-open) No. 62-175182/1987 corresponding to EP-225,701A). The plasmid pNTK26 was similarly cleaved with restriction enzymes ClaI and HindIII, and the smaller fragment was removed. Then, the resulting fragment was ligated to the above 1.1-kb ClaI-HindIII fragment containing the A-MuLV LTR region with T4 DNA ligase, and the ligation mixture was used for the transformation of E. coli DH1 to give ampicillin-resistant transformant E. coli DH1/pNTL145. Plasmid pNTL145 was isolated from the transformant thus obtained (FIG. 7).

REFERENCE EXAMPLE 6

(Construction of Polypeptide (I) Expression Vector for Animal Cells)

A 0.86-kb EcoRI-AhaIII fragment containing the regions coding for the signal peptide, the propeptide and the polypeptide (I) in the polypeptide (I) cDNA was isolated from the plasmid pHNT2 obtained in reference Example 2 (as to the location of the AhaIII site, refer to FIGS. 4 and 5). The 5'-terminus (EcoRI) of the resulting fragment was made flush with Klenow fragment, and then a XhoI linker pCCTC-GAGG was ligated to each terminus thereof with T4 ligase, followed by treatment with XhoI. Thus, a 0.86-kb XhoI fragment was obtained.

Figure 8:
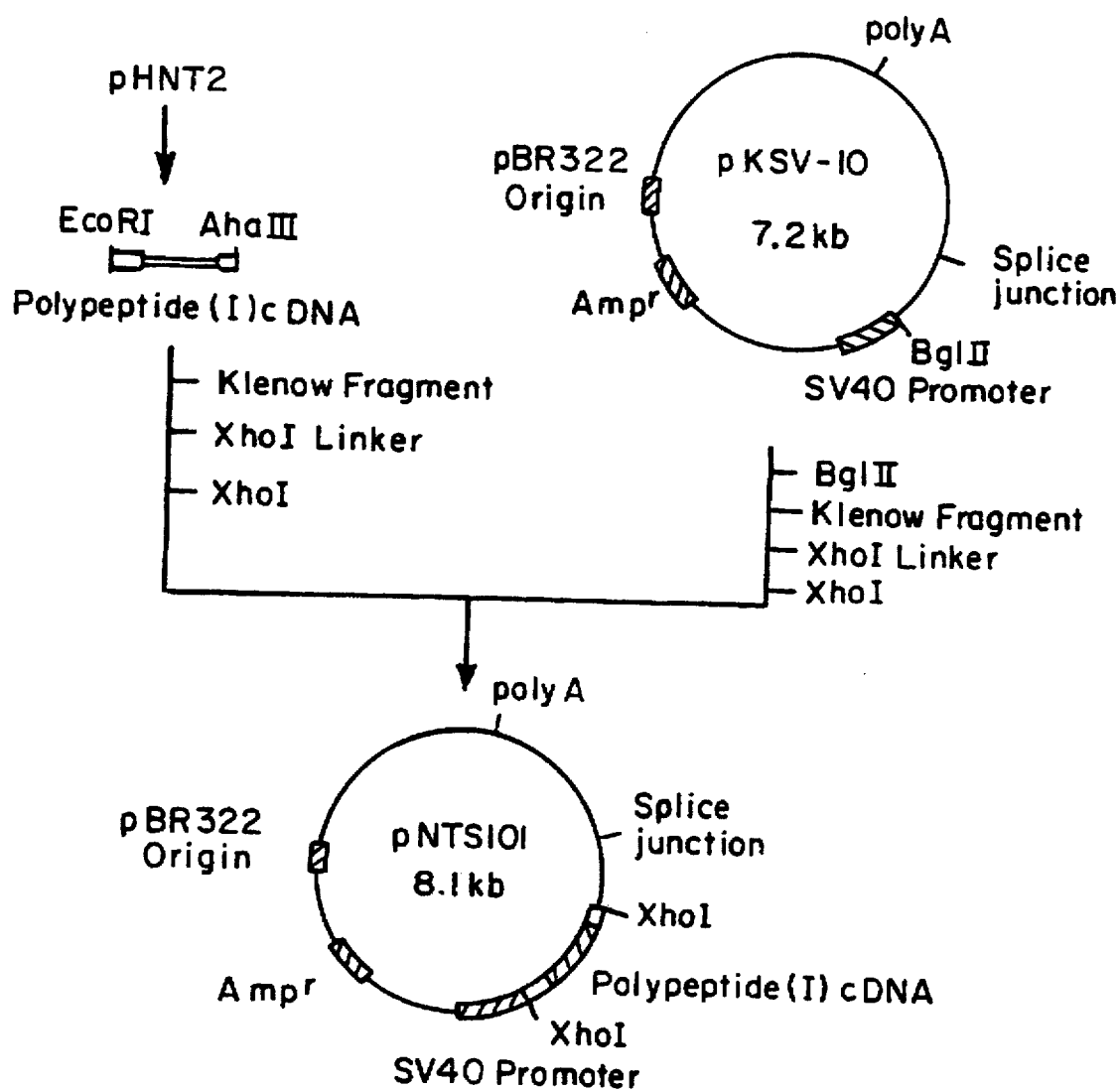
FIG. 8 is a schematic representation showing the construction of polypeptide (I) expression vector pNTS101 for animal cells obtained in Reference Example 6.

The expression vector pKSV-10 (Pharmacia) for animal cells was cleaved with restriction enzyme BglII, and then both ends (XhoI) of the resulting fragment was made flush with Klenow fragment. The XhoI linker (previously described) was added thereto, and this fragment was ligated to the above 0.86-kb XhoI fragment with T4 DNA ligase. The ligated fragment was used to transform E. coli DH1. Plasmid pNTS101 was isolated from the resulting ampicillin-resistant transformant E. coli DH1/pNTS101 (FIG. 8).

REFERENCE EXAMPLE 7

(Expression of Polypeptide (I) cDNA in Animal Cells)

Monkey COS-7 cells were cultivated in monolayer in Dulbecco's modified Eagle's medium (DMEM medium) (Flow Laboratories) containing 10% fetal calf serum, followed by exchanging the medium for the same medium. After 4 hours from the exchange, calcium phosphate gels containing the expression vector pTB389, 10 µg of the polypeptide (I) expression vector pNTK26 and the polypeptide (I) expression vector pNTL145, respectively, were prepared according to the method known in the art [Graham et al., Virology 52, 456 (1973)], and added to cells to obtain transformants COS-7/pTB389, COS-7/pNTK26 and COS-7/pNTL145, respectively. These cells were cultivated in a carbon dioxide incubator for 4 hours, and then treated with glycerol [Gorman et al., Science 221, 551 (1983)], followed by cultivation for 3 days. Cultures after cultivation were centrifuged to obtain culture supernatants. PC12 cells were cultivated in the presence of the respective supernatants according to the method described in Brain Research 133, 350 (1977) and Experimental Cell Research 145, 179 (1983), and the proportions of cells whose neutrites outgrew to at least twice the diameter of the cells were calculated. The results are shown in Table 2.

TABLE 2

| Vector | Culture Supernatant (µl) | Proportion of Cells with Neurites Twice the Size of Cell Diameter (%) |
|---|---|---|
| pTB389 | 40 | 11 |
| pNTK26 | 40 | 17 |
| pNTL145 | 40 | 20 |

Using a culture supernatant obtained by a method similar to that described above, the effect on acetylcholine (ACh) content of co-cultured septal and basal forebrain neurons [M. Kakihana and M. Suno, Nerve Chemistry 27, 166 (1988)] was investigated.

Septum and basal forebrain were dissected from 17-day fetal rat brains, and nerve cells were isolated therefrom in accordance with the method of Hatanaka et al. [Develop. Brain Res. 30, 47 (1986)]. The cells were seeded on a 48-well plate pretreated with 100 µg/ml of poly-L-ornithine at a density of about $1 \times 10^6$ cells/cm$^2$/well, and cultivated in 500 µl of a serum-free DME/F12/N2 medium for 24 hours. After removing the medium by suction, 500 µl of DME/F12/10% FCS and the supernatant of the specimen were added. After 2 days, the medium was exchanged for 750 µl of the same medium, and the supernatant was added again, followed by cultivation for 2 days. The supernatant was added sequentially. Namely, 50 µl of the supernatant was added for the former two days and 75 µl thereof for the latter two days to give a final concentration of 10%. When mouse NGF (7S-NGF) purchased from Wako Pure Chemical Industries was used, it was diluted with 0.1% ovalbumin/PBS, and 10 µl thereof was added.

After 4 days from the addition of the supernatant, the medium was removed by suction, and 500 µl of cooled 0.3N PCA and 20 to 60 pmoles/20 µl of ethylhomocholine (EHC) were added thereto for measurement of ACh. After gentle stirring, 500 µl of the solution was transferred to an Eppendolf microtube. Subsequent operations were carried out in accordance with the previously reported methods, and the amount of ACh was measured by use of a high-performance liquid chromatography/electrochemical detector (HPLC/ECD) system. After extraction of ACh, the cells were dissolved in 500 µl of 1N NaOH, and the amount of protein was assayed (Bio-RAD protein assay). Dunnett's t-test was used for statistical treatment.

The results are shown in Table 3.

TABLE 3

| Experiment | Sample | Number of Wells | Amount of Acetylcholine (pmol/mg protein) |
|---|---|---|---|
| 1 | Mouse NGF 0 ng/ml | 6 | 492 ± 31 |
|   | Mouse NGF 0.1 ng/ml | 6 | 526 ± 14 |

TABLE 3-continued

| Experiment | Sample | Number of Wells | Amount of Acetylcholine (pmol/mg protein) |
|---|---|---|---|
|   | Mouse NGF 1 ng/ml | 6 | 600 ± 31 |
|   | Mouse NGF 10 ng/ml | 6 | 775 ± 29 |
|   | Supernatant (10%) of COS-7/pTB 389 | 6 | 582 ± 22 |
|   | Supernatant (10%) of COS-7/pNTL 145 | 6 | 652 ± 13 |
| 2 | Supernatant (10%) of COS-7/pTB389 | 4 | 332 ± 7 |
|   | Supernatant (10%) of COS-7/pNTL 145 | 6 | 395 ± 7 |

REFERENCE EXAMPLE 8

(Production of Polypeptide (I) by Escherichia coli)

Escherichia coli BL21(DE3) [Gene 56, 125 (1987)] was transformed by the polypeptide (I) expression vector pENGFT102 obtained in Reference Example 3 and T7 lysozyme expression vector pLysS to obtain transformant Escherichia coli BL21(DE3)/pLysS, pENGFT102 (IFO 14903, FERM BP-2529).

The transformant E. coli BL21(DE3)/pLysS, pENGFT102 was cultivated in LB medium [1% tryptone (Difco), 0.5% yeast extract, 0.5% NaCl] containing 50 µg/ml of ampicillin, 10 µg/ml of chloramphenicol and 0.2% glucose at 37° C. for 16 hours with shaking. The culture (12.5 ml) was transferred into a 1-liter Erlenmeyer flask containing 250 ml of the same medium, and cultivated at 30° C. for 3 hours with shaking. Thereupon, the Klett value of the culture reached 170. Isopropyl-$\beta$-D(-)-thiogalactopyronoside was added to this culture at a final concentration of 0.1 mM, and the resulting solution was cultivated at 30° C. for 3 hours with shaking. Cells collected from 30 µl of the culture solution thus obtained were suspended in 30 µl of sample buffer [Laemmli, Nature 227, 680 (1970)], and heated at 100° C. for 5 minutes, followed by electrophoresis on 16% polyacrylamide gels containing 0.1% SDS. The proteins on the gels were transferred to a nitrocellulose membrane according to the method of Burnette [Analytical Biochemistry 112, 195 (1981)], and then, Western blotting was carried out using the rabbit anti-mouse NGF antibody (Collaborative Research Inc. U.S.A.) and the affinity-purified HRP-linked goat anti-rabbit IgG (Bio RAD, U.S.A.). As a result, the polypeptide (I) having a molecular weight of 15 kilodaltons (kDa) was detected.

When gels obtained in a manner similar to that described above and subjected to electrophoresis were dyed with Coomassie Brilliant Blue, a 15-kDa protein corresponding to the polypeptide (I) was detected, and the amount of the 15-kDa protein produced was estimated to be about 10% of the total proteins.

REFERENCE EXAMPLE 9

(Isolation of Polypeptide (I))

The culture (3.75 liter) of the transformant E. coli BL21 (DE3)/pLysS, pENGFT102 obtained in Reference Example 8 was centrifuged to give 17 g (wet) of cells. The cells were suspended in 375 ml of 50 mM Tris-HCl (pH 8.0) and freeze-thawed, followed by treatment with a sonic oscillator (Kaijo Denki, 2A, 2 minutes) 3 times. The broken cell suspension was centrifuged, and the resulting precipitate was dissolved in 60 ml of 5M guanidine hydrochloride-5 mM EDTA-1 mM PMSF-0.1 mM APMSF-20 mM dithiothreitol (DTT)-50 mM sodium phosphate buffer (pH 6.0). The solution thus obtained was applied to a Sephacryl S-200 column equilibrated with 2M guanidine hydrochloride-5 mM EDTA-0.1 mM APMSF-5 mM DTT-25 mM sodium phosphate buffer (pH 6.0), and the fractions in which the polypeptide (I) was detected by the Western blotting method (previously described) were collected (volume=300 ml). This solution was concentrated by use of an ultrafilter equipped with a YM5 membrane (Amicon), and 50 ml of the resulting concentrated solution was applied to the Sephacryl S-200 column as described above. Thus, 164 ml of a solution containing 328 mg of the purified polypeptide (I) was obtained. The purity was investigated by SDS-polyacrylamide gel electrophoresis. As a result, it was confirmed that the resulting purified polypeptide (I) was substantially homogeneous.

A solution containing the above purified polypeptide (I) was loaded onto an Ultrapore RPSC column (0.46×7.5 cm, Altex), and chromatographed by high-performance liquid chromatography (HPLC) with a trifluoroacetic acid-acetonitrile eluent solvent system to obtain the homogeneous polypeptide (I). The N-terminal amino acid sequence of the resulting polypeptide (I) was determined with a gas phase protein sequencer (Model 470A, Applied Biosystems). Consequently, the N-terminal amino acid sequence of the purified polypeptide (I) agreed with the N-terminal amino acid sequence of the polypeptide (I) deduced from the nucleotide sequence of cDNA except that a methionine residue was added to the N-terminus (Table 4).

The amino acid composition of the purified sample obtained above was determined by the ninhydrin method. The results obtained show that, the observed values substantially agreed with the theoretical values calculated from the polypeptide (I) to the N-terminus of which a methionine residue was added (Table 5).

TABLE 5

| Amino Acid Composition | | |
|---|---|---|
| | Experimental[1] Value | Theoretical[2] Value |
| Asp | 10.3 | 11 |
| Thr | 8.3 | 9 |
| Ser | 10.0 | 12 |
| Glu | 11.0 | 11 |
| Pro | 1.8 | 2 |
| Gly | 7.9 | 8 |
| Ala | 5.1 | 5 |
| Cys | 5.9 | 6 |
| Val | 8.4 | 9 |
| Met | 1.0 | 1 |
| Ile | 6.8 | 7 |

TABLE 5-continued

| Amino Acid Composition | | |
|---|---|---|
| | Experimental[1] Value | Theoretical[2] Value |
| Leu | 5.1 | 5 |
| Tyr | 5.2 | 5 |
| Phe | 1.1 | 1 |
| Lys | 9.6 | 10 |
| His | 3.6 | 4 |
| Arg | 9.3 | 10 |
| Trp | 3.6 | 4 |

[1]Calculated taking Glu as 11.
[2]Calculated with a methionine residue was added to the N-terminus of the polypeptide (I).

A solution (protein concentration: 2 mg/ml) containing the above purified polypeptide (I) was diluted with 2M guanidine hydrochloride-5 mM EDTA-0.1 mM APMSF-5 mM DTT-25 mM sodium phosphate buffer (pH 6.0) so as to give a protein concentration of 10 µg/ml. The diluted solution was dialyzed against a 50-fold amount of 1 mM EDTA-50 mM NaHCO$_3$-Na$_2$CO$_3$ (pH 10.0) at 4° C. for 16 hours and further dialyzed against the freshly introduced same buffer for 4 hours. The effect of the resulting dialyzed fluid on PC12 cells was examined in accordance with the method described in Brain Research 133. 350 (1979) and Experimental Cell Research 145, 179 (1983). As a result, it was observed that 6% of the PC12 cells had neurites by addition of the inner dialyzed fluid, and 2% thereof had neurites having a length of at least 2 times the diameter of

TABLE 4

| | N-terminal Amino Acid Sequence | | | | | | | | | |
|---|---|---|---|---|---|---|---|---|---|---|
| | 1 | 2 | 3 | 4 | 5 | 6 | 7 | 8 | 9 | 10 |
| Sequence Determined from Purified Sample | Met | Tyr | Ala | Glu | His | Lys | Ser | His | Arg | Gly |
| Sequence Deduced from cDNA | Tyr | Ala | Glu | His | Lys | Ser | His | Arg | Gly | Glu | the cell body. On the other hand, with 1 mM EDTA-50 mM NaHCO$_3$-Na$_2$CO$_3$ (pH 10.0) as a control, not more than 0.5% of the cells had neurites.

EXAMPLE 1

(Immunization)

BALB/c mice (female, 8 weeks old) were intradermally injected with 10 µg of the antigen polypeptide (I) (obtained in Reference Example 9) which was dissolved in 0.4 ml of Freund's complete adjuvant (Difco). Three weeks later, the mice were intradermally given again 10 µg of the antigen polypeptide (I) dissolved in 0.4 ml of Freund's complete adjuvant. 3 weeks later, a similar additional immunization was carried out. Two weeks after the additional immunization, the mice were intravenously inoculated with 10 µg of the polypeptide (I) dissolved in physiological saline.

EXAMPLE 2

(1) Cell Fusion

Three days after the final inoculation, the spleens were removed from the mice immunized in Example 1 to obtain cells to be used for cell fusion. These cells were suspended in a medium prepared by mixing Iscove medium with Ham F-12 medium in a ratio of 1:1. This mixed medium is hereinafter referred to as IH medium.

Mouse myeloma cells P3-X63-Ag·SUI were subcultured in RPMI 1640 medium containing 10% fetal calf serum under an atmosphere of 5% carbon dioxide and 95% air.

Cell fusion was carried out in accordance with the method established by Kohler and Milstein [G. Kohler and C. Milstein, Nature 256, 495 (1975)]. The above myeloma cells ($2.9 \times 10^7$ cells) were mixed with the immunized lymphocytes ($5 \times 10^8$ cells) obtained by the above method, and the mixture was centrifuged. Then, 0.3 ml of 45% polyethylene glycol 6000 (hereinafter referred to as PEG 6000) dissolved in IH medium was dropwise added thereto. The PEG 6000 solution was preheated to 37° C. and slowly added. After 5 minutes, the IH medium preheated to 37° C. was added thereto at a rate of 0.5 ml/min until the total volume was 10 ml. The solution was then centrifuged at room temperature at 600 rpm for 15 minutes to remove a supernatant. The resulting cell precipitate was suspended in 200 ml of IH medium containing 20% calf serum. The suspension was seeded in a 96-well microtiter plate (Nunc) in an amount of 200 μl/well. One day later, IH medium (containing 20% calf serum) supplemented with HAT ($1 \times 10^{-4}$M hypoxanthine, $4 \times 10^{-7}$M aminopterin, $1.6 \times 10^{-5}$M thymidine) was added to the microtiter plate in an amount of 100 μl/well. The IH medium supplemented with HAT is hereinafter referred to as HAT medium. Further every 3 days, one-half the amount of the medium was exchanged for HAT medium. The cells which thus grew were hybrid cells.

(2) Screening for Antibody-Producing Cells

Preliminarily, a hybrid cell culture supernatant was added in an amount of 100 μl/well to a 96-well polystyrene microtiter plate to which the polypeptide (I) had been fixed, and incubated at 37° C. for 1 hour. After removal of the resulting supernatant and washing, the horseradish peroxidase (HRP)-labeled anti-mouse IgG goat antibody (Kappel) was added as the second antibody, and incubated at 37° C. for 1 hour. After the second antibody was removed and the wells were thoroughly washed, coloring reaction was conducted by adding a reaction substrate (EIA method). By this method, the high antibody titer was observed in 4 wells.

(3) Cloning of Hybrid Cells

The cells in these wells were spread to 0.5 cell per well on a 96-well microtiter plate on which $10^4$ cells/well of mouse thymocytes had preliminarily been spread as vegetative cells, and cloning was carried out. As a result, there were obtained 4 clones, MoAb4-2 cells (IFO 50241, FERM BP-2908), MoAb46-31 cells (IFO 50242, FERM BP-2909), MoAb82-4 cells (IFO 50243, FERM BP-2910) and MoAb148-62 cells (IFO 50244, FERM BP-2911). The deposits FERM BP-2908, FERM BP-2909, FERM BP-2910 and FERM BP-2911 were each made on May 15, 1990 under the Budapest Treaty at Fermentation Research Institute Agency of Industrial Science and Technology, 1-3, Higashi 1 chome, Tsukuba-shi, Ibaraki-ken 305, Japan.

Table 6 shows the results of measurement of the antibody titer in the supernatants of these cells.

TABLE 6

| Dilution | Culture supernatant | | | | | |
|---|---|---|---|---|---|---|
| | MoAb 4-2 | MoAb 46-31 | MoAb 82-4 | Moab 148-62 | Parent strain myeloma cell | Polypeptide (1) immunized mouse serum |
| X 80 | 2.48 | 2.42 | 0.61 | 1.51 | 0.02 | 2.47 |
| X 160 | 2.35 | 2.14 | 0.42 | 1.37 | 0.02 | 2.42 |
| X 1280 | 0.81 | 0.58 | 0.11 | 0.65 | 0.01 | 0.99 |
| X 2560 | 0.49 | 0.34 | 0.07 | 0.43 | 0.01 | 0.57 |

In Table 6, the values show the absorption at a wavelength of 492 nm.

The cloned cells were stored in liquid nitrogen, adding dimethyl sulfoxide to IH medium containing 20% calf serum to a concentration of 10%.

EXAMPLE 3

(Immunoglobulin Class of Monoclonal Antibodies)

The mouse antibodies obtained in Example 2 were reacted with various immunoglobulin samples by a subclass detecting kit (Bio RAD). The results are shown in Table 7.

TABLE 7

| Immuno-globulin sample | Monoclonal antibody of this invention | | | |
|---|---|---|---|---|
| | MoAb4-2 | MoAb46-31 | MoAb82-4 | MoAb148-62 |
| IgG1 | − | − | + | + |
| IgG2a | − | − | − | − |
| IgG2b | + | + | − | − |
| IgG3 | − | − | − | − |
| IgM | − | − | − | − |
| IgA | − | − | − | − |

In Table 7, "+" indicates that the reaction is positive, and "−" indicates that the reaction is negative.

Table 7 shows that the antibodies produced by MoAb4-2 and MoAb46-31 belong to IgG2b in immunoglobulin and that the antibodies produced by MoAb82-4 and MoAb148-62 belong to IgG1 in immunoglobulin.

EXAMPLE 4

(Preparation of Ascites Containing Monoclonal Antibodies)

For each of the hybridomas MoAb4-2, MoAb46-31, MoAb82-4 and MoAb148-62, $2 \times 10^6$ cells were injected into the mice preliminarily given intraperitoneally 0.5 ml of mineral oil. After 10 days, 2 to 4 ml/mouse of ascites was collected. From the respective hybridomas were obtained monoclonal antibodies MoAb4-2, MoAb46-31, MoAb82-4 and MoAb148-62.

EXAMPLE 5

(Purification of Antibodies from Ascites)

According to the method described in Example 4, each of the monoclonal antibodies MoAb4-2, MoAb46-31, MoAb82-4 and MoAb148-62 were injected into 5 mice to obtain 20 to 30 ml of ascites. The ascites was centrifuged at 2,000 rpm for 10 minutes in a centrifuge (Hitachi, Japan) to remove cells, and then centrifuged at 22,000 rpm for 2 hours at 4° C. in a Spinco SW28 rotor (Beckman, U.S.A.) to remove insoluble proteins, fats and the like. Ammonium sulfate was added to the supernatant to a saturated concentration of 40%, followed by gently stirring in ice for 1 hour. The precipitate was centrifuged at 4° C. at 15,000 rpm for 30 minutes by a Serval SS34 rotor (du Pont, U.S.A.). After recovery, the precipitate was dissolved in 10 mM potassium phosphate buffer (pH 6.8), and purified using a hydroxyapatite column (HCA-column). In this case, 10 mM potassium phosphate buffer (pH 6.8) was used as an initiation buffer, and 500 mM sodium phosphate buffer was used as an elution buffer. Elution was effected by a linear gradient from the initiation buffer to the elution buffer. The eluted antibodies were stored at 4° C.

EXAMPLE 6

(Preparation of HRP-Labeled Antibody)

(1) The monoclonal antibody MoAb4-2 obtained in Example 5 was concentrated to 2 mg/ml or more, and then dialyzed against 0.2 M phosphate buffer (pH 7.0). An N,N'-dimethylformamide (DMF) solution of S-acetylmercaptosuccinic anhydride (Aldrich, U.S.A.) was added in an amount of 50 µl to 0.7 ml of 4.9 mg/ml monoclonal antibody MoAb4-2 to give a concentration of 11.5 mg/ml. The air in a reaction vessel was replaced with nitrogen gas. The vessel was sealed, followed by stirring at room temperature for 1 hour to introduce an SH group or SH groups into the monoclonal antibody. Unreacted S-acetylmercaptosuccinic anhydride was inactivated by treatment with 130 µl of 0.2M Tris-HCl (pH 7.0), 13 µl of 0.2M EDTA and 130 µl of 2M hydroxylamine (pH 7.0) at room temperature for 10 minutes. The monoclonal antibody MoAb4-2 was subjected to gel filtration using a Sephadex G-25 column (1 cm diameter×80 cm, Pharmacia, Sweden) (flow rate: 20 ml/hour).

(2) In 1.4 ml of 0.1M phosphate buffer (pH 6.8) was dissolved 10 mg of horseradish peroxidase (HRP, Grade I, Behringer Manheim, West Germany). Concurrently, 14 mg of N-hydroxysuccinimide ester of N-(4-carboxycyclohexylmethyl)maleimide was dissolved in 335 µl of DMF, and 100 µl of the resulting solution was added to the HRP solution. The air in a reaction vessel was replaced with nitrogen gas. The vessel was sealed, followed by stirring at room temperature for 1 hour. Then, the maleimide group-introduced HRP fractions were separated by gel filtration using the Sephadex G-25 column (previously described).

(3) 6 ml of the SH group-introduced antibody MoAb4-2 fractions obtained in (1) and 2 ml of the maleimide group-introduced HRP fractions obtained in (2) were mixed with each other. The mixture was concentrated to 1 ml under reduced pressure using a collodion bag (Sartorius, West Germany), followed by reaction at 4° C. for 20 hours. After the reaction, the HRP-introduced antibody was applied on an Ultrogel AcA44 column (1 cm diameter×80 cm, LKB, Sweden) for fractionation (flow rate: 10 ml/hour). Of the eluted peak fractions, the fractions having the highest HRP number per molecule of antibody showed 2.4 HRP/antibody.

EXAMPLE 7

(Assay of Polypeptide (I) by EIA Using Monoclonal Antibody)

The monoclonal antibody MoAb82-4 obtained in Example 5 was diluted to 10 µg/ml with carbonate buffer (pH 9.6), and the above diluted antibody was poured in an amount of 100 µl/well into an immunoplate (Nunc, Denmark), followed by standing at 4° C. overnight to adsorb the monoclonal antibody to the plate. After removing the antibody not reacted, the plate was washed with PBS 3 times, and PBS containing 0.01% merthiolate and 5% bovine serum albumin (BSA) was added thereto in an amount of 300 µl/well, followed by standing at 4° C. overnight.

The polypeptide (I) obtained in Reference Example 9 was diluted with PBS containing 1% BSA. Concurrently, the BSA solution was removed from the plate obtained above, and the plate was washed with PBS 5 times. Then, the above diluted polypeptide (I) was added thereto in an amount of 100 µl/well to adsorb the polypeptide (I) to the plate at 4° C. overnight. After removing the polypeptide (I) not reacted, the plate was washed with PBS 5 times. The HRP- linked antibody (HRP-MoAb4-2) obtained in Example 6 was diluted 1/1,000 with 1% BSA, and the diluted antibody solution was added in an amount of 100 µl/well to the plate, followed by reaction at room temperature for 2 hours. After removing the antibody solution, the plate was washed 10 times with PBS, and a peroxidase substrate (Sigma) was added in an amount of 100 µl/well thereto to develop color for comparative assay.

Figure 9:
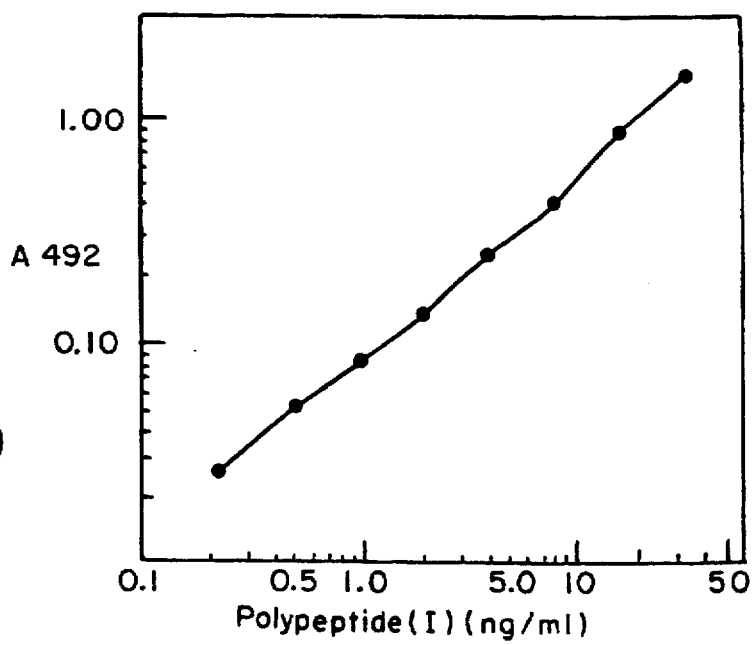
FIG. 9 is a graph showing the results of determination of the polypeptide (I) by EIA in Example 7, using monoclonal antibody MoAb82-4 obtained in Example 5 and HRP-MoAb4-2 obtained in Example 6.

FIG. 9 shows a detection curve of the polypeptide (I). In this graph, the concentration of the polypeptide (I) added is plotted as abscissa and the absorbance of the color developed with HRP-MoAb4-2 as ordinate. This graph reveals that the polypeptide (I) having a concentration of 0.5 ng/ml can be detected.

EXAMPLE 8

(Determination of Antigen Recognition Sites)

The antigen recognition sites of the 4 antibodies purified in Example 4 were examined by competitive binding inhibition experiments. As competitive peptides, there were used synthetic peptides pep1: Tyr-Ala-Glu-His-Lys-Ser-His-Arg-Gly-Glu-Tyr-Ser-Val-Cys and pep2: Cys-Ala-Leu-Ser-Arg-Lys-Ile-Gly-Arg.

The synthetic peptides were diluted with a PBS solution containing 5% BSA to a concentration of 100 µg/ml or 0.39 µg/ml. For the purified monoclonal antibodies obtained in Example 4, MoAb4-2 and MoAb46-31 were diluted to 0.05 µg/ml, MoAb82-4 was diluted to 12.5 µg/ml, and MoAb148-62 was diluted to 0.78 µg/ml so that the amount of antibody showed 0.7 to 1.0 at an absorbance of 493 nm. As a diluent, the PBS solution containing 5% BSA was used. The diluted competitive peptide was added to the diluted antibody solution. After stirring, the mixture was maintained at 37° C. for 30 minutes.

The amount of antibody not bound in this solution was assayed by the HIA shown in Example 7.

The results obtained when the synthetic peptides were used are shown in FIGS. 10 to 13. FIGS. 10 to 13 show the results for the monoclonal antibodies MoAb4-2, MoAb46-31, MoAb82-4 and MoAb148-62, respectively. Referring to these figures, open circles (—o—) when pep1 was used, and closed circles (—●—) when pep2 was used. In these figures, the absorbance (at a wavelength of 493 nm) of a color coupler is plotted as ordinate.

Figure 10:
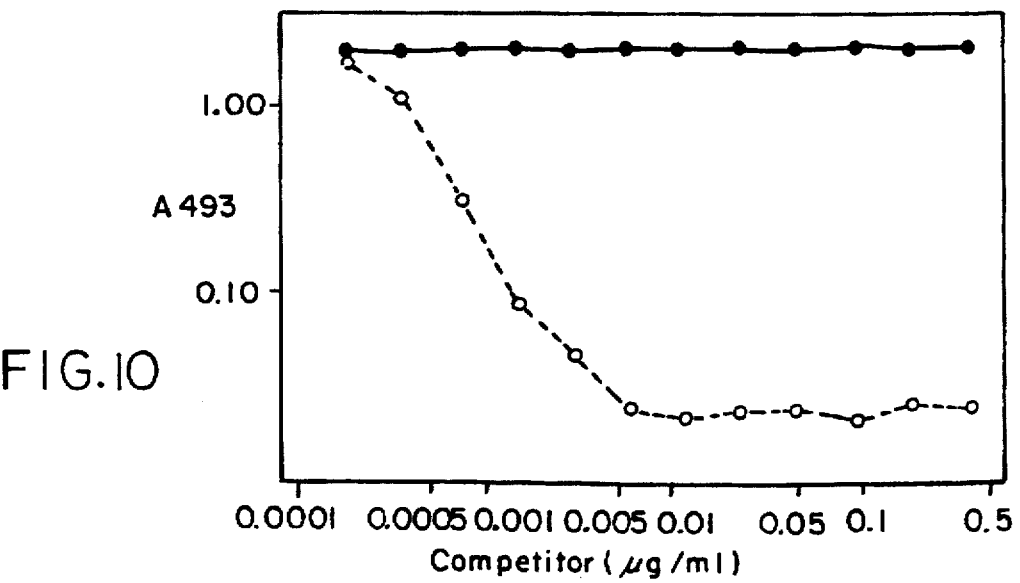
FIG. 10 is a graph showing the results of competitive binding inhibition of various peptides to monoclonal antibody MoAb4-2, obtained in Example 8.
Figure 11:
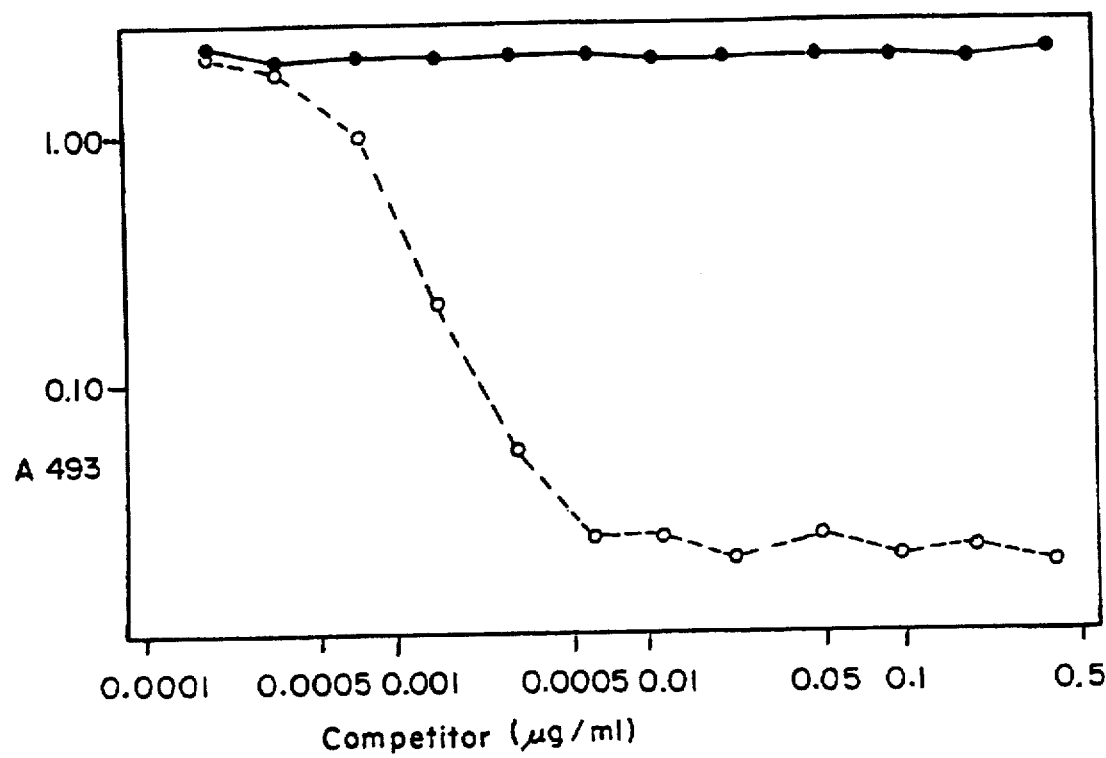
FIG. 11 is a graph showing the results of competitive binding inhibition of various peptides to monoclonal antibody MoAb46-31, obtained in Example 8.

FIGS. 10 and 11 show that the monoclonal antibodies MoAb4-2 and MoAb46-31 recognized the N-terminal 1st to 14th amino acid region of the polypeptide (I).

Figure 12:
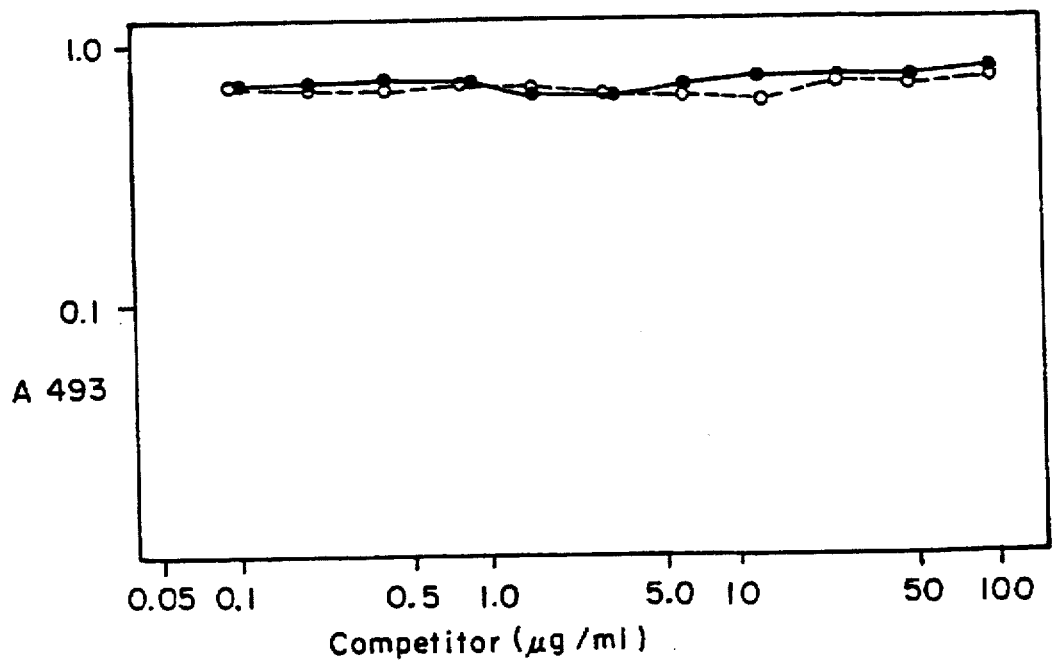
FIG. 12 is a graph showing the results of compeptitive binding inhibition of various peptides to monoclonal antibody MoAb82-4, obtained in Example 8.
Figure 13:
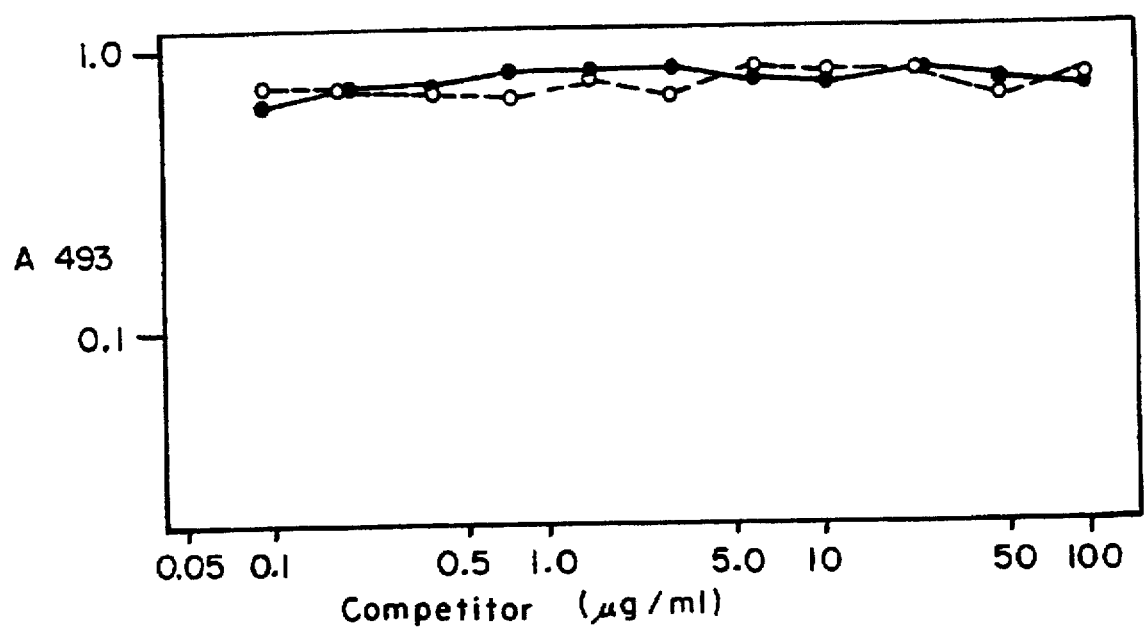
FIG. 13 is a graph showing the results of compeptitive binding inhibition of various peptides to monoclonal antibody MoAb84-62, obtained in Example 8.
Figure 14:
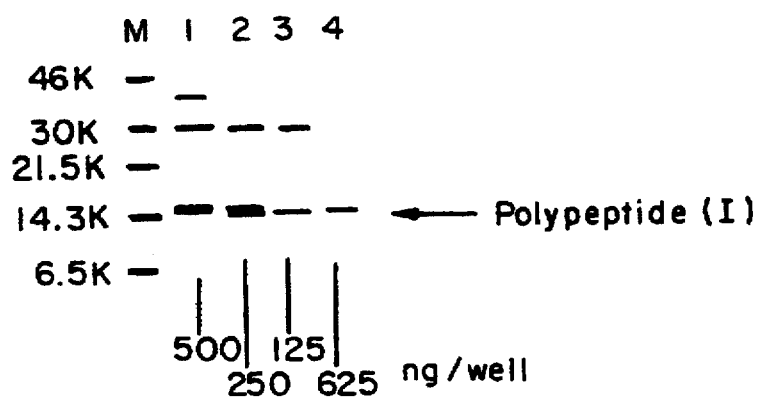
FIG. 14 is a diagram showing the results of Western blotting analysis using monoclonal antibody MoAb4-2 obtained in Example 5.

FIGS. 12 and 13 show that the monoclonal antibodies MoAb82-4 and MoAb148-62 did not suffer from the inhibition by these synthetic peptides. This reveals that the monoclonal antibodies MoAb82-4 and MoAb148-62 recognized amino acids other than the N-terminal 1st to 14th amino acid region and the C-terminal 1st to 9th region.

From the above, the recognition sites of the 4 monoclonal antibodies are summarized as shown in Table 8.

TABLE 8

|  | Monoclonal antibody | | | |
| --- | --- | --- | --- | --- |
|  | 4-2 | 46-31 | 82-4 | 148-62 |
| pep1 | + | + | − | − |
| pep2 | − | − | − | − |

In Table 8, "+" indicates that the competitive hindrance occurred, and "−" indicates that the competitive hindrance did not occur.

EXAMPLE 9

(Detection of Human Polypeptide (I) by Western Blotting)

The polypeptide (I) obtained according to the method described in Reference Example 9 was subjected to 15% acrylamide gel electrophoresis [U. K. Laemmli, *Nature* 227, 680–685 (1970)], and then transferred to a nitrocellulose membrane using Sartblot (Sartorius) [J. Kyshse-Anderson, *Journal of Biochemical and Biophysical Methods* 10, 203–209 (1984)]. This membrane was washed with TBS [20 mM Tris-HCl (pH 7.5), 0.5M NaCl] twice for 5 minutes at a time, and then allowed to stand at room temperature for 1 hour in TBS containing 5% BSA to block unreacted portions on the membrane. The membrane was then washed with TBS containing 0.05% Tween 20 (TTBS) 3 times for 5 minutes at a time. The monoclonal antibody MoAb4-2, MoAb46-31, MoAb82-4 or MoAb148-62 obtained in Example 4 was diluted 1,000 times with TTBS containing 5% BSA, in which the above nitrocellulose membrane was immersed. Then, the reaction was conducted at room temperature for 1 hour. The reaction solution was removed and the membrane was washed with TTBS 3 times for 5 minutes at a time. Then, a second antibody, alkaline phosphatase-labeled anti-mouse IgG goat serum (Bio RAD, U.S.A.), diluted 2,000 times with TTBS containing 5% BSA was added thereto, followed by reaction at room temperature for 1 hour. The membrane was washed with TTBS 3 times for 5 minutes at a time and further with TBS 2 times for 5 minutes at a time. Then, the membrane was reacted at room temperature for 15 minutes with 66 μl of NBT (nitro blue tetrazolum, 50 mg/ml in 70% dimethylformamide) and 33 μl of BCIP (5-bromo-4-chloro-3- indolyl phosphate, 50 mg/ml in dimethylformamide) (Promega, U.S.A.) dissolved in AP buffer [100 mM Tris-HCl (pH 9.5), 100 mM NaCl, 5 mM $MgCl_2$] as color-producing agents. FIG. 15 shows the results of Western blotting when the monoclonal antibody MoAb4-2 was used as the first antibody. 500 ng of the polypeptide (I) was electrophoresed and transferred in lane 1, 250 ng of the polypeptide (I) in lane 2, 125 ng of the polypeptide (I) in lane 3 and 62.5 ng of the polypeptide (I) in lane 4. "M" represents a marker, and the figures on the left side represents its molecular weight.

When MoAb46-31, MoAb82-4 and MoAb148-62 were used in lieu of the above MoAb4-2, the polypeptide (I) was also detected.

EXAMPLE 10

(Preparation of Anti-N-Terminal Peptide Antibody)

(1) Synthesis of N-Terminal Peptide

Synthesis of H-Tyr-Ala-Glu-His-Lys-Ser-His-Arg-Gly-Glu-Tyr-Ser-Val-Cys-OH

This peptide was synthesized by a solid-phase synthesis method using an automatic peptide synthesizer (Model 430A, Applied Biosystems, U.S.A.). "Standard-1" was used as a program. The basic synthesis course conformed to the method described in R. B. Merrifield, *Adv. Enzymol.* 32, 221–296 (1969). Boc-Cys(MeBzl)-pAM-p (0.5 mmole/g) was used as a resin, and the synthesis was conducted in turn from the carboxyl terminus. The following Boc-amino acids were used: Boc-Val, Boc-Ser(Bzl), Boc-Tyr(Br-Z), Boc-Glu (OBzl), Boc-Gly, Boc-Arg(Tos), Boc-His(Tos), Boc-Lys(Cl-Z) and Boc-Ala. After the peptide was synthesized up to the amino-terminus Tyr, the peptide resin was taken out of the synthesizer and dried.

To 1 g of the peptide resin were added 1.5 ml of p-cresol and 0.5 ml of 1,2-ethanedithiol, and about 8 ml of liquid hydrogen fluoride was further added thereto, followed by reaction at 0° C. for 2 hours. After completion of the reaction, hydrogen fluoride was removed in a desiccator under reduced pressure. The peptide resin was washed with diethyl ether containing 0.1% mercaptoethanol and subsequently with diethyl ether to remove almost all included reagents. The peptide was extracted with 10 ml of 3% acetic acid and the resin contained in the extract was removed by filtration. The filtrate was purified by gel filtration using a Sephadex G-25 column (2.8×60 cm) (detection wavelength: 280 nm, solvent: 3% acetic acid, flow rate: 40 ml/hour).

The fractions containing the peptide were collected and lyophilized. The resulting powder sample was further purified by reverse-phase high performance liquid chromatography under the following conditions:

Column: YMC Pack, A-324 ODS, 10×250 mm

Column temperature: 25° C.

Eluent A: 0.1% trifluoroacetic acid—99.9% distilled water

Eluent B: 0.1% trifluoroacetic acid—99.9% acetonitrile

Elution program: 0 minute (90% A+10% B) 30 minutes (60% A+40% B)

Flow rate: 2 ml/minute

Detection wavelength: 230 nm

Main peak fractions eluted at a retention time of 23.0 minutes under these conditions were collected and passed through a Bio RAD AG1X8 column (AcOH type, 1.8×5 cm). The washings were also collected and acetonitrile was removed by distillation, followed by lyophilization. Thus, 56 mg of a white powder was obtained. The desired peptide thus obtained exhibited a single peak at 23.0 minutes under the same conditions as with the above high performance liquid chromatography.

The determination of free SH groups by the method of Elman [G. L. Elman, *Arch. Biochem. Biophys.* 82, 70–77 (1959)]: 114%

Anal. for amino acids: Ser 1.65(2); Glu 2.13(2); Gly 1.00(1); Ala 1.04(1); 1/2Cys 0.82(1); Val 1.03(1); Tyr 1.97 (2); Lys 0.95(1); His 1.72(2); Arg 1.00(1) Recovery: 74%

1/2Cys was determined by the performic acid oxidation method. The values in parentheses show the theoretical values.

(2) preparation of Conjugate of N-Terminal Peptide with Hemocyanin

The N-terminal peptide (5 mg) obtained in (1) and hemocyanin (10 mg) were dissolved in 4 ml of 0.2M phosphate buffer (pH 7.3), and 400 μl of 2.5% glutaraldehyde cooled in ice water was added drop by drop thereto with stirring. After stirring under ice cooling for 3 hours, the dialysis against distilled water was carried out to obtain a conjugate of the N-terminal peptide with hemocyanin.

(3) Preparation of Conjugate of N-Terminal Peptide with Bovine Serum Albumin

Bovine serum albumin (BSA) (132 mg) was dissolved in 3 ml of 0.1M phosphate buffer (pH 7.5) (solution A). Concurrently, 11.2 mg of N-(γ-maleimidobutyloxy) succinimide (GMBS) was dissolved in 200 µl of dimethylformamide (solution B). Solution B was added dropwise to solution A while stirring with a stirrer, and the mixture solution was subjected to reaction at 30° C. for 30 minutes. Then, the reaction product was purified by a Sephadex G-25 column (1.5×20 cm) using 0.1M phosphate buffer (pH 6.5)-0.1M NaCl as an eluent to obtain maleimide group-introduced bovine serum albumin.

The peptide (5 mg) obtained in (1) was dissolved in 0.1M phosphate buffer-5 mM EDTA, and the maleimide group-introduced bovine serum albumin (20 mg) was added thereto (5 ml or less in total volume), followed by reaction at 30° C. for 60 minutes. PBS was added thereto to a total volume of 12 ml to obtain a conjugate of the N-terminal peptide with the bovine serum albumin.

(4) Preparation of Anti-Polypeptide (I) N-Terminal Peptide Antibody

The conjugate of the N-terminal peptide with hemocyanin obtained in (2) was thoroughly mixed with Freund's complete adjuvant, and the resulting mixture was subcutaneously injected into the rabbits. Thereafter, the conjugate of the N-terminal peptide with the bovine serum albumin obtained in (3) was mixed with Freund's incomplete adjuvant, and the resulting mixture was injected into the same rabbits at two week intervals. The blood collected from the rabbits immunized by the method described above was centrifuged to obtain an anti-polypeptide (I) N-terminal peptide antibody.

EXAMPLE 11

(Preparation of Anti-C-Terminal Peptide Antibody)

(1) Synthesis of C-Terminal Peptide

Synthesis of H-Cys-Ala-Leu-Ser-Arg-Lys-Ile-Gly-Arg-OH

The C-terminal peptide was synthesized in a manner similar to that in Example 10.

Boc-Arg(Tos)-PAM-P (0.5 mmole/g) was used as a resin, and the synthesis was conducted in turn from the carboxyl terminus. As Boc-amino acids, there were used Boc-Gly, Boc-Ile, Boc-Lys(Cl-Z), Boc-Arg(Tos), Boc-Ser(Bzl), Boc-Leu, Boc-Ala and Boc-Cys(MeBzl). The resulting peptide resin was treated with hydrogen fluoride and purified as in Example 10 to obtain 200 mg of a white powder, the desired product. This peptide was eluted at 12.6 minutes as a single sharp peak under the conditions of high performance liquid chromatography described in Example 10.

The determination of free SH groups by the method of Elman [G. L. Elman, *Arch. Biochem. Biophys.* 82, 70–77 (1959)]: 106%

Anal. for amino acids: Ser 0.86(1); Gly 0.96(1); Ala 1.00(1); Ile 1.00(1); Leu 1.01(1); Lys 1.05(1); Arg 2.06(2) Recovery: 68%

(2) Preparation of Conjugate of C-Terminal Peptide with Hemocyanin

Using the C-terminal peptide obtained in (1), a conjugate of the C-terminal peptide with hemocyanin was obtained in a manner similar to that in Example 10 (2).

(3) Preparation of Conjugate of C-Terminal Peptide with Bovine Serum Albumin

Using the C-terminal peptide obtained in (1), a conjugate of the C-terminal peptide with bovine serum albumin was obtained in a manner similar to that in Example 10 (3).

(4) Preparation of Anti-Polypeptide (I) C-Terminal Peptide Antibody

The conjugate of the C-terminal peptide with hemocyanin obtained in (2) was thoroughly mixed with Freund's complete adjuvant, and the resulting mixture was subcutaneously injected into the rabbits. Thereafter, the conjugate of the C-terminal peptide with the bovine serum albumin obtained in (3) was mixed with Freund's incomplete adjuvant, and the resulting mixture was injected into the same rabbits at two week intervals. The blood collected from the rabbits immunized by this method was centrifuged to obtain an anti-polypeptide (I) C-terminal peptide antibody.

According to the present invention, the polypeptide (I) can be easily and accurately isolated and purified by the antibodies to the polypeptide (I) or its partial peptides. The antibodies can assist in elucidation of the functional mechanism of the polypeptide (I), and pioneer their application for medicines. Their industrial promise is therefore high. Further, in this invention, the antibodies can be obtained by using the partial partial peptides of the polypeptide (I) as a portion of the antigen. In this case, the starting materials can be obtained by simple methods such as chemical synthesis because the partial can be chemccally synthesized. The antibodies to the polypeptide (I) or its partial peptides can be produced more simply than the mature protein of the polypeptide (I) whose isolation and purification are quite complicated. Hence, simple methods for detecting and assaying the polypeptide (I) can be provided.

The following references, which are referred to for their disclosures at various points in this application, are incorporated herein by reference.

Japanese Patent Unexamined Publication No. 1-193654/1989 (EP Application No. 90 104 419.8 and U.S. patent application Ser. No. 07/488,696)

The Peptide, 1, Academic Press, New York, U.S.A. (1966)

Izumiya et al., Peptide Synthesis, Maruzen (1975)

Izumiya et al., Fundamentals and Experiments of Peptide Synthesis, Maruzen (1985)

Course of Biochemical Experiments 1, Chemistry of Proteins, pages 255 to 332, edited by Biochemical Society of Japan, Tokyo Kagaku Dojin (1976)

Nature 256, 495 (1975)

J. Immun. Method 80, 55 (1985)

J. Am. Med. Assoc. 199, 549 (1967)

Proc. Natl. Acad. Sci. U.S.A. 80, 3513–3516 (1983)

Metabolism 8, 696 (1971)

Analytical Biochemistry 112, 195 (1981)

Nature 227, 680 (1970)

Molecular Cloning, A Laboratory Manual, Cold Spring Harbor Laboratory (1982)

Nucl. Acid. Res. 9, 309 (1981)

Nature 303, 821 (1983)

Proceedings of National Academy of Sciences, U.S.A. 68, 2417 (1971)

Nature 302, 538 (1983)

Gene 56, 125 (1987)

Japanese Patent Unexamined Publication (Laid-open) No. 64-2572/1989 corresponding to EP-251,244A Japanese Patent Unexamined Publication (Laid-open) No.62-175182/1987 corresponding to EP-225,701A Virology 52, 456 (1973)

Science 221, 551 (1983)

Brain Research 133, 350 (1977)

Experimental Cell Research 145, 179 (1983)

Nerve Chemistry 27, 166 (1988)
Develop. Brain Res. 30, 47 (1986)
Journal of Biochemical and Biophysical Methods 10, 203–209 (1984)
Adv. Enzymol. 32, 221–296 (1969)
Arch. Biochem. Biophys. 82, 70–77 (1959)

What is claimed is:

1. An antibody to a peptide consisting of 12 to 14 successive amino acids of a sequence represented by:

TyrAlaGluHisLysSerHisArgGlyGluTyrSerValCys, or 8 to 9 successive amino acids of a sequence represented by:

CysAlaLeuSerArgLysIleGlyArg.

2. An antibody obtained by using a conjugate of a peptide with a carrier protein as an immunogen, said peptide consisting of 12 to 14 successive amino acids of a sequence represented by:

TyrAlaGluHisLysSerHisArgGlyGluTyrSerValCys, or 8 to 9 successive amino acids of a sequence represented by:

CysAlaLeuSerArgLysIleGlyArg.

3. A method for detecting a polypeptide having an amino acid sequence represented by formula (1):

TyrAlaGluHisLysSerHisArgGlyGluTyrSerValCys AspSerGluSer-
LeuTrpValThrAspLysSerSerAlaIle AspIleArgGlyHisGlnValThr-
ValLeuGlyGluIleLys ThrGlyAsnSerProValLysGlnTyr-
PheTyrGluThrArg
CysLysGluAlaArgProValLysAsnGlyCysArgGlyIle AspAspLy-
sHisTrpAsnSerGlnCysLysThrSerGlnThr TyrValArgAla-
LeuThrSerGluAsnAsnLysLeuValGly TrpArgTrpIleArg-
IleAspThrSerCysValCysAlaLeu SerArgLysIleGlyArg     (1)

using an antibody to a peptide consisting of 12 to 14 successive amino acids of a sequence represented by:

TyrAlaGluHisLysSerHisArgGlyGluTyrSerValCys, or 8 to 9 successive amino acids of a sequence represented by:

CysAlaLeuSerArgLysIleGlyArg, said method comprising: (a) incubating a sample containing the polypeptide with the antibody under conditions that allow binding to occur, and (b) detecting the specific binding of the antibody to the polypeptide, said binding being indicative of the presence of the polypeptide in said sample.

4. A cloned hybridoma comprising a spleen cell of a mammal and a lymphoid cell of the mammal, said spleen cell of the mammal being immunized with (i) a peptide consisting of 12 to 14 successive amino acids of a sequence represented by:

TyrAlaGluHisLysSerHisArgGlyGluTyrSerValCys, or 8 to 9 successive amino acids of a sequence represented by:

CysAlaLeuSerArgLysIleGlyArg, or (ii) with a conjugate of the peptide with a carrier protein.

* * * * *

UNITED STATES PATENT AND TRADEMARK OFFICE
CERTIFICATE OF CORRECTION

PATENT NO. : 5,712,100
DATED : January 27, 1998
INVENTOR(S) : K. Nakahama, et al.

It is certified that error appears in the above-identified patent and that said Letters Patent is hereby corrected as shown below:

On the title page: Item

[63] "Aug. 29, 1990" should read --Aug. 28, 1990--

Signed and Sealed this

Twenty-fifth Day of April, 2000

Attest:

Q. TODD DICKINSON

*Attesting Officer*  *Director of Patents and Trademarks*